(12) United States Patent
Viscomi et al.

(10) Patent No.: US 9,452,157 B2
(45) Date of Patent: Sep. 27, 2016

(54) PHARMACEUTICAL COMPOSITIONS COMPRISING RIFAXIMIN AND AMINO ACIDS, PREPARATION METHODS AND USE THEREOF

(71) Applicant: ALFA WASSERMANN SPA, Bologna (IT)

(72) Inventors: Giuseppe Claudio Viscomi, Bologna (IT); Laura Chelazzi, Bologna (IT); Fabrizia Grepioni, Bologna (IT); Dario Braga, Bologna (IT); Maddalena Kindt, Bologna (IT)

(73) Assignee: Alfa Wassermann S.P.A, Alanno (Pescara) (IT)

( * ) Notice: Subject to any disclaimer, the term of this patent is extended or adjusted under 35 U.S.C. 154(b) by 0 days.

(21) Appl. No.: 13/935,331

(22) Filed: Jul. 3, 2013

(65) Prior Publication Data

US 2014/0079783 A1    Mar. 20, 2014

(30) Foreign Application Priority Data

Jul. 6, 2012 (IT) ................ BO2012A0368

(51) Int. Cl.
| | |
|---|---|
| *A61K 31/437* | (2006.01) |
| *A61K 9/00* | (2006.01) |
| *A61K 9/16* | (2006.01) |
| *A61K 9/28* | (2006.01) |
| *A61K 31/198* | (2006.01) |
| *A61K 31/405* | (2006.01) |
| *A61K 31/4172* | (2006.01) |
| *A61K 47/18* | (2006.01) |
| *C07D 498/22* | (2006.01) |
| *G01N 33/15* | (2006.01) |

(52) U.S. Cl.
CPC ........... *A61K 31/437* (2013.01); *A61K 9/0095* (2013.01); *A61K 9/1617* (2013.01); *A61K 9/2866* (2013.01); *A61K 31/198* (2013.01); *A61K 31/405* (2013.01); *A61K 31/4172* (2013.01); *A61K 47/183* (2013.01); *C07D 498/22* (2013.01); *G01N 33/15* (2013.01)

(58) Field of Classification Search
None
See application file for complete search history.

(56) References Cited

U.S. PATENT DOCUMENTS

| | | | |
|---|---|---|---|
| 4,263,404 A | 4/1981 | White et al. | |
| 4,267,274 A | 5/1981 | White et al. | |
| 4,341,785 A | 7/1982 | Marchi et al. | |
| 4,557,866 A | 12/1985 | Cannata et al. | |
| 4,816,568 A | 3/1989 | Hamilton, Jr. et al. | |
| 5,284,512 A | 2/1994 | Koskan et al. | |
| 5,356,625 A | 10/1994 | Ying | |
| 5,840,332 A | 11/1998 | Lerner et al. | |
| 7,045,620 B2 | 5/2006 | Viscomi et al. | |
| 7,709,634 B2 | 5/2010 | Kothakonda et al. | |
| 7,902,206 B2 | 3/2011 | Viscomi et al. | |
| 7,906,542 B2 | 3/2011 | Viscomi et al. | |
| 7,915,275 B2 | 3/2011 | Viscomi et al. | |
| 7,923,553 B2 | 4/2011 | Viscomi et al. | |
| 8,067,429 B2 | 11/2011 | Gushurst et al. | |
| 8,158,644 B2 | 4/2012 | Viscomi et al. | |
| 8,158,781 B2 | 4/2012 | Viscomi et al. | |
| 8,173,801 B2 | 5/2012 | Viscomi et al. | |
| 8,193,196 B2 | 6/2012 | Viscomi et al. | |
| 8,227,482 B1 | 7/2012 | Parent et al. | |
| 8,318,763 B2 | 11/2012 | Viscomi et al. | |
| 8,404,704 B2 | 3/2013 | Viscomi et al. | |
| 8,518,949 B2 | 8/2013 | Viscomi et al. | |
| 8,569,326 B2 | 10/2013 | Gushurst et al. | |
| 2003/0059471 A1 | 3/2003 | Compton et al. | |
| 2005/0036968 A1 | 2/2005 | Shen | |
| 2005/0196418 A1 | 9/2005 | Yu et al. | |
| 2005/0272754 A1 | 12/2005 | Viscomi et al. | |
| 2008/0262024 A1 | 10/2008 | Viscomi et al. | |
| 2009/0028940 A1 | 1/2009 | Jahagirdar et al. | |
| 2009/0082558 A1 | 3/2009 | Kothakonda et al. | |
| 2009/0234114 A1* | 9/2009 | Viscomi et al. | ............ 540/457 |
| 2009/0312357 A1 | 12/2009 | Rao et al. | |
| 2010/0174064 A1 | 7/2010 | Gushurst et al. | |
| 2010/0298428 A1 | 11/2010 | Yacoby-Zeevi et al. | |
| 2011/0065740 A1* | 3/2011 | Forbes et al. | ................ 514/279 |
| 2011/0086871 A1 | 4/2011 | Viscomi et al. | |

(Continued)

FOREIGN PATENT DOCUMENTS

| | | |
|---|---|---|
| CA | 1215976 A1 | 12/1986 |
| CA | 1218650 A1 | 3/1987 |

(Continued)

OTHER PUBLICATIONS

Hirano et al., J. Phys. Chem. B, 114, pp. 13455-13462 (2010).*

(Continued)

*Primary Examiner* — Bethany Barham
*Assistant Examiner* — Barbara Frazier
(74) *Attorney, Agent, or Firm* — Steinfl & Bruno LLP

(57) ABSTRACT

The present invention relates to rifaximin compositions comprising amino acids, characterized in that they increase rifaximin solubility in aqueous solutions and are useful in the treatment of disease wherein amino acids and rifaximin are efficacious. The present invention also relates to pharmaceutical compositions comprising rifaximin or one of the pharmaceutically acceptable salts thereof and one or more amino acid(s), wherein the molar ratio between the amino acid(s) and rifaximin is from 1:1 to 10:1, together with pharmaceutically acceptable excipients. The present invention further relates to rifaximin crystals obtained by dissolving rifaximin and amino acids in solutions formed by ethanol/water and evaporating the solution.

34 Claims, No Drawings

(56) References Cited

U.S. PATENT DOCUMENTS

| | | |
|---|---|---|
| 2011/0105550 A1 | 5/2011 | Gushurst et al. |
| 2012/0035202 A1 | 2/2012 | Viscomi et al. |
| 2012/0076857 A1 | 3/2012 | Gushurst et al. |
| 2012/0116071 A1 | 5/2012 | Rao et al. |
| 2012/0202989 A1 | 8/2012 | Viscomi et al. |
| 2012/0203000 A1 | 8/2012 | Viscomi et al. |
| 2012/0207833 A1 | 8/2012 | Parent et al. |
| 2012/0214989 A1 | 8/2012 | Viscomi et al. |
| 2012/0264774 A1 | 10/2012 | Parent et al. |
| 2013/0004576 A1 | 1/2013 | Viscomi et al. |
| 2013/0066079 A1 | 3/2013 | Gushurst et al. |
| 2013/0281697 A1 | 10/2013 | Viscomi et al. |
| 2013/0287692 A1 | 10/2013 | Viscomi et al. |
| 2013/0289269 A1 | 10/2013 | Viscomi et al. |
| 2013/0310410 A1 | 11/2013 | Viscomi et al. |
| 2014/0011828 A1 | 1/2014 | Gushurst et al. |
| 2014/0235662 A1 | 8/2014 | Viscomi et al. |
| 2015/0073007 A1 | 3/2015 | Viscomi et al. |

FOREIGN PATENT DOCUMENTS

| | | | |
|---|---|---|---|
| CH | 571064 A5 | 12/1975 | |
| EP | 0161534 B1 | 11/1985 | |
| EP | 0935417 B1 | 8/1999 | |
| EP | 1557421 B1 | 7/2005 | |
| EP | 1676847 B1 | 7/2006 | |
| EP | 1676848 A1 | 7/2006 | |
| EP | 1698630 B1 | 9/2006 | |
| EP | 2011486 A1 | 1/2009 | |
| EP | 2208730 A1 | 7/2010 | |
| EP | 2210893 A1 | 7/2010 | |
| EP | 2420226 A1 | 2/2012 | |
| EP | 2421869 B1 | 2/2012 | |
| EP | 2542225 B1 | 1/2013 | |
| GB | 1317830 A | 5/1973 | |
| IT | 1154655 B1 | 11/1981 | |
| IT | 1349654 | 10/2003 | |
| WO | 9000553 A1 | 1/1990 | |
| WO | 9200302 A1 | 1/1992 | |
| WO | 9312812 A1 | 7/1993 | |
| WO | 9313792 A1 | 7/1993 | |
| WO | 9319773 A1 | 10/1993 | |
| WO | 0010512 A2 | 3/2000 | |
| WO | 0214323 A2 | 2/2002 | |
| WO | 0236542 A1 | 5/2002 | |
| WO | 0243732 A1 | 6/2002 | |
| WO | 2005044823 A2 | 5/2005 | |
| WO | 2006094662 A1 | 9/2006 | |
| WO | 2008029208 A1 | 3/2008 | |
| WO | 2008035109 A1 | 3/2008 | |
| WO | 2008155728 A1 | 12/2008 | |
| WO | 2009008005 A1 | 1/2009 | |
| WO | 2009008006 A2 | 1/2009 | |
| WO | 2009108730 A2 | 9/2009 | |
| WO | 2010044093 A1 | 4/2010 | |
| WO | 2010067072 | 6/2010 | |
| WO | 2010067072 A1 | 6/2010 | |
| WO | 2010122436 A1 | 10/2010 | |
| WO | 2011050397 A1 | 5/2011 | |
| WO | 2011051971 A2 | 5/2011 | |
| WO | 2011061516 A2 | 5/2011 | |
| WO | 2011061519 A2 | 5/2011 | |
| WO | 2011061748 A1 | 5/2011 | |
| WO | 2011080691 A1 | 7/2011 | |
| WO | 2011088688 A1 | 7/2011 | |
| WO | WO 2011/088688 * | 7/2011 | ............... A61K 9/14 |
| WO | 2011103120 A1 | 8/2011 | |
| WO | 2011107970 A2 | 9/2011 | |
| WO | 2011110930 A2 | 9/2011 | |
| WO | 2011153444 A1 | 12/2011 | |
| WO | 2011156897 A2 | 12/2011 | |
| WO | 2012009387 A1 | 1/2012 | |
| WO | 2012009388 A1 | 1/2012 | |
| WO | 2012035283 A1 | 3/2012 | |
| WO | 2012035544 A2 | 3/2012 | |
| WO | 2012076832 A1 | 6/2012 | |
| WO | 2012109605 A2 | 8/2012 | |
| WO | 2012150561 A1 | 11/2012 | |
| WO | 2012155981 A1 | 11/2012 | |
| WO | 2012156533 A1 | 11/2012 | |
| WO | 2012156951 A1 | 11/2012 | |
| WO | 2013112809 A2 | 8/2013 | |
| WO | 2013185211 A1 | 12/2013 | |
| WO | 2014091432 A1 | 6/2014 | |
| WO | 2015014984 A1 | 2/2015 | |

OTHER PUBLICATIONS

Machine translation, WO 2011/088688 (2011).*
XIFAXAN®, Physicians' Desk Reference, Oct. 3, 2007, pp. 2790-2791, 62, Thomson Healthcare, Montvale XP002601190.
Rifaximin, Jan. 1, 2009, pp. 4955-4957, European Pharmacopoeia 6.5.
Rifaximin, Jan. 1, 2011, pp. 3459-3460, European Pharmacopoeia 7.1.
Bacchi A. et al., Sampling rifamycin conformational variety by cruising through crystal forms: implications for polymorph screening and for biological models., Oct. 1, 2008, pp. 1725-1735, 32 (10), New J. Chem.
Henwood S.Q. et al., Solubility and dissolution properties of generic rifampicin raw materials., Apr. 1, 2000, pp. 403-408, 26 (4), Drug Dev. Ind. Pharm.
Morris K.R. et al., Theoretical approaches to physical transformations of active pharmaceutical ingredients during manufacturing processes., May 16, 2001, pp. 91-114, 48 (1), Adv. Drug Deliv. Rev.
Morris K.R., Structural aspects of hydrates and solvates. In:"Polymorphism in pharmaceutical solids" edited by H.G. Brittain, Jan. 1, 1999, pp. 125-181, 95, Drugs and the Pharmaceutical Sciences, Chap. 4.
Pelizza G. et al., Polymorphism of rifampicin., Jul. 1, 1977, pp. 471-481, 32 (7), Farmaco Sci.
Rodríguez-Spong B. et al., General principles of pharmaceutical solid polymorphism: a supramolecular perspective., Feb. 23, 2004, pp. 241-274, 56 (3), Adv. Drug Deliv. Rev.
Vippagunta S.R. et al., Crystalline solids., May 16, 2001, pp. 3-26, 48 (1), Adv. Drug Deliv. Rev.
Viscomi G.C. et al., Crystal forms of rifaximin and their effect on pharmaceutical properties., Jan. 1, 2008, pp. 1074-1081, 10, CrystEngComm.
Qing Li et al., Solvothermal growth of vaterite in the presence of ethylene glycol, 1,2-propanediol and glycerin., Mar. 1, 2002, pp. 357-362, 236 (1-3), J. Crystal Growth.
Hirano A, et al., Arginine-assisted solubilization system for drug substances: solubility experiment and simulation., Sep. 3, 2010, pp. 13455-13462, 114, J Phys Chem B.
Andreas Hotter, Preparation of Raw Rifaximin and of Dried Raw Rifaximin According to Example 1 of EP 1698630—Andreas Hotter, May 29, 2015, pp. 1-6.
Arthur Pichler, Analysis via Powder X-Ray Diffraction of Current NORMIX® Tablets—Arthur Pichler, May 29, 2015, pp. 1-9.
Dana Hoffmann, Rifaximin, Oral Bioavailability Study in Dogs of Four Different Polymorphic Isoforms—Dana Hoffmann, pp. 1-4, Jun. 3, 2015.
Mino R. Caira, Crystalline Polymorphism of Organic Compounds, Jan. 1, 1999 pp. 1 and 164-208.
Henck Jan-Olav, Polymorphie von Arzneistoffen Eine wirtschaftliche Herausforderung?, Jan. 1, 1997, pp. 165-169, 59, Pharmind, English Summary Included.
Braga D et al., The Structure-Property Relationship of Four Crystal Forms of Rifaximin, Aug. 9, 2012, pp. 6404-6411, 14, CrystEngComm.
Cruz-Cabeza et al. Conformational polymorphism, Dec. 18, 2013, pp. 2170-2191.
Keith J. Guillory, Generation of polymorphs, hydrates, solvates, and amorphous solids, Jan. 1, 1999, pp. 183-226.
Bauer et al., Ritonavir: an extraordinary example of conformational polymorphism, Mar. 10, 2001, pp. 859-866, Pharmaceutical Research, vol. 18, No. 6.

(56) References Cited

OTHER PUBLICATIONS

Brittain, Polymorphism and solvatomorphism 2009, 2011, pp. 1260-1279, Journal of Pharmaceutical Sciences, vol. 100, No. 4.
Corti et al., Application of derivative resolution of UV spectra to the quality control of rifaximine and its possible impurities, Jan. 1, 1992, pp. 76-79, Pharm. Acta. Helv. vol. 67, No. 3.
Rossi et al., NMR studies of a new class of rifaximin-derived molecules: rifaximin OR (Open ring), Jan. 1, 1996, pp. 268-269, J. Chem. Research (S).
Martini et al., Solution structure of rifaximin and its synthetic derivative rifaximin OR determined by experimental NMR and theoretical simulation methods., May 1, 2004, pp. 2163-2172, Bioorg. Med. Chem. 12.
Swanepoel, Quality evaluation of generic drugs by dissolution test: changing the USP dissolution medium to distinguish between active and non-active mebendazole , May 1, 2003, pp. 345-349, European Journal of Pharmaceutics and Biopharmaceutics 55.
Liu et al., Structure elucidation of two unknown oxydic degradation impurities of rifaximin, Jan. 1, 2011, pp. 3251-3256, Asian Journal of Chemistry, vol. 23, No. 7.
Agrawal et al., Solid-state characterization of rifampicin samples and its biopharmaceutic relevance., Jun. 1, 2004, pp. 127-144, European Journal of Pharmaceutical Sciences 22.
Son et al., A new respirable form of rifampicin, Feb. 13, 2011, pp. 366-376, European Journal of Pharmaceutics and Biopharmaceutics 78.
Blandizzi et al., Impact of crystal polymorphism on the systemic bioavailability of rifaximin, an antibiotic acting locally in the gastrointestinal tract, in healthy volunteers, Dec. 16, 2014, pp. 1-11, Drug Design, Development and Therapy.
Saifee et al., Drug polymorphism: a review, Dec. 1, 2009, pp. 291-306, International Journal of Health Research, 2(4).
Kremer et al., Re-emergence of tuberculosis: strategies and treatment., Feb. 1, 2002, pp. 153-157, Exper. Opin. Investig. Drugs 11(2).
Marchese et al., In vitro activity of rifaximin, metronidazole and vancomycin against Clostridium difficile and the rate of selection of spontaneously resistant mutant, Jul. 1, 2000, pp. 253-266, Chemotherapy, 46.
TicinumLab, TicinumLab example 9 of EP0161534 "Synthesis of 4-deoxy-4'methyl-pyrido-[1',2':1,2]imidazo[5,4 c]ryfamicin SV", May 13, 2010, pp. 1-2.
TicinumLab, TicinumLab example 7 of EP0161534 "Synthesis of 4-deoxy-4'methyl-pyrido-[1',2':1,2]imidazo[5,4-c]ryfamicin SV" May 13, 2010, pp. 1-2.
Zach System, Synthesis of rifaximin obtained according to examples 7 and 9 reported in EP 0161534—Zach System, May 13, 2010, pp. 1-16.
Brufani M. et al., X-ray crystal structure of 4-deoxy-3'-bromopyrido[1',2'-1,2]imidazo[5,4-c]rifamycin S., J. Antibiot. (Tokyo), 37 (12), pp. 1623-1627, Dec. 1, 1984.
Cellai L. et al., A study of structure-activity relationships in 4-deoxypyrido[1',2'-1,2]imidazo[5,4-c]rifamycin SV derivatives by electron spectroscopy for chemical analysis and 1H NMR, Mol. Pharmacol., 27 (1), pp. 103-108, Jan. 1, 1985.
Cellai L. et al., Structure-activity relationships in 4-deoxypyrido[1',2'-1,2]imidazo[5,4-c]rifamycin SV derivatives, Il Farmaco, 44 (2), pp. 97-107, Feb. 1, 1989.
Marchi E. et al., 4-Deoxypyrido[1',2':1,2]imidazo[5,4-c]rifamycin SV derivatives. A new series of semisynthetic rifamycins with high antibacterial activity and low gastroenteric absorption, J. Med. Chem., 28 (7), pp. 960-963, Jul. 1, 1985.
Martinelli E. et al., Rifamycin R, a novel metabolite from a mutant of Nocardia mediterranea., J. Antibiot. (Tokyo), 31 (10), pp. 949-951, Oct. 1, 1978.
Early Search Report and opinion provided to European Patent Office on Dec. 5, 2012 for priority ITBO20120368. 10 pages.
International Search Report issued by the European Patent Office on Dec. 9, 2013 for the application PCT/IB2013/055448 in the name of Alfa Wassermann S.P.A. 6 pages.
Rao R.N. et al., On-line 2D-LC-ESI/MS/MS determination of rifaximin in rat serum, Biomed. Chromatogr., 23 (11), pp. 1145-1150, Nov. 1, 2009.
Rossi C. et al., NMR Investigation of a New Semisynthetic Bioactive Compound, Bull. Magn. Reson., 18 (1-2), pp. 87-90 , Jan. 1, 1996.
Sensi P. et al., Rifomycin, a new antibiotic—preliminary report, Farmaco Sci., 14 (2), pp. 146-147, Feb. 1, 1959.
Sensi P., A family of new antibiotics, the rifamycins. In: "Research Progress in Organic-Biological and Medicinal Chemistry"—Società Editoriale Farmaceutica, Edited by U. Gallo, et al., 1, pp. 337-421, Jan. 1, 1964.
Venturini A.P., Pharmacokinetics of L/105, a new rifamycin, in rats and dogs, after oral administration, Chemotherapy, 29 (1), pp. 1-3, Jan. 1, 1983.
Stradi R. et al., Structural elucidation of the Rifaximin Ph. Eur. Impurity H, J. Pharm. Biomed. Anal., 51 (4), pp. 858-865, Mar. 11, 2010.
Italian Product Label for NORMIX (rifaximin), Apr. 23, 1985. 6 pgs.
Rifaximin—Intrinsic Dissolution—Experimental Data, Apr. 1, 2009. 1 pg.

* cited by examiner

PHARMACEUTICAL COMPOSITIONS COMPRISING RIFAXIMIN AND AMINO ACIDS, PREPARATION METHODS AND USE THEREOF

FIELD OF THE INVENTION

This invention relates to compositions comprising rifaximin and one or more amino acids, their method of preparation and their medical use.

BACKGROUND OF THE INVENTION

Rifaximin (INN; see The Merck Index, XIII ed., 8304) is a semi-synthetic non-aminoglycoside derived from rifamycin. More precisely, it is a pyrido-imidazo rifaximin, described and claimed in the Italian patent IT 1154655, whereas the European patent EP 0161534 describes a process for its production starting from rifamycin 0.

Rifaximin is (S-S, 16Z, 18E, 20S, 21S, 22R, 23R, 24R, 25S, 26S, 27S, 28E)-5, 6, 21, 23, 25-pentahydroxy-27-methoxy-2, 4, 11, 16, 20, 22, 24, 26-octamethyl-2,7-(epoxy pentadeca-[1,11,13] trienimino)-benzofuro [4,5-e]-pyrido[1, 2-(alpha)]-benzimidazole-1,15(2H) dione, 25-acetate), and is represented in Formula 1.

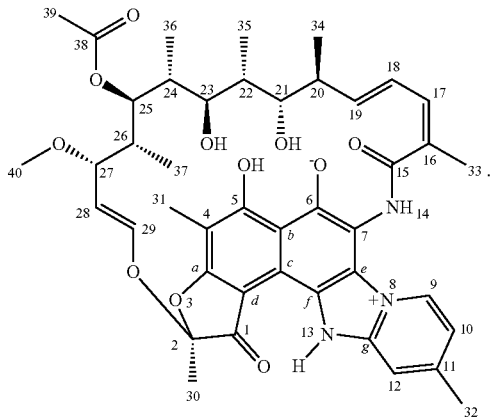

Formula 1

Rifaximin is also currently sold under the trademark Normix®, Rifacol® and Xifaxan®.

Rifaximin is an antibiotic usually used for local action with a broad spectrum of action against Gram-positive and Gram-negative bacteria and aerobic and anaerobic organisms. Rifaximin has an excellent safety profile and it is characterized for a non-systemic absorption.

Rifaximin is used for the treatment of bowel infections caused by non-enteroinvasive bacteria, traveler's diarrhea, enteritis, dysentery, bowel inflammations such as, for instance, Crohn's disease (CD), ulcerous recto-colitis, irritable bowel syndromes (IBS), paucities, small intestinal bacterial overgrowth (SIBO), diverticular syndromes; pathologies directly or indirectly deriving from bowel infections, such as for instance hepatic encephalopathy, or which can be used in the pre- and post-operative prophylaxis of bowel infections.

U.S. Pat. No. 4,557,866 describes a process for the synthesis of pyrido-imidazo rifaximins comprising the reaction of rifamycin 0 with 4-methyl-2-aminopyridine.

EP 1557421B1, EP 1676847 B1, EP 1676848 B1 and U.S. Pat. No. 7,045,620 B2 describe polymorphic forms of rifaximin (INN), called rifaximin α, rifaximin β, and a poorly crystalline form called rifaximin γ. These forms can be obtained by hot-dissolving raw rifaximin in ethyl alcohol and by inducing subsequent crystallization of the product by addition of water at a given temperature and for a fixed time. The crystallization is then followed by a drying step carried out under controlled conditions, e.g., until a predefined water content is obtained, and the X-ray diffraction profile corresponds to one observed for one or more of the aforesaid rifaximin forms.

These patents also describe processes for the transformation from one polymorphic form to another, such as obtaining polymorph α by dehydration of polymorph β or polymorph γ; obtaining polymorph γ starting from polymorph α and the preparation of polymorph β by hydration of polymorph α.

U.S. Pat. No. 7,906,542 B2 describes pharmaceutical compositions comprising polymorphic forms of rifaximin α, β and γ.

EP 1682556 A2 describes polymorphic forms of rifaximin α, β and γ and their different in vivo absorption and dissolution profiles.

U.S. Pat. No. 7,915,275 B2 describes the use of pharmaceutical compositions comprising polymorphic forms of rifaximin α, β and γ for the treatment of bowel infections.

WO 2008/155728 describes a process for obtaining amorphous rifaximin by hot-dissolving raw rifaximin in absolute ethyl alcohol and then collecting after precipitation by cooling rifaximin under amorphous form.

Amorphous forms of rifaximin and processes for their obtainment are described in US 2009/312357 and US 2009/0082558, in particular US 2009/0082558 describes that amorphous rifaximin is obtained after precipitating by addition of water to a rifaximin solution in organic solvent.

WO 2009/108730 describes polymorphic forms of rifaximin (form ζ, form γ-1 (ζ), form α-dry, form η form ι, form β-1, form β-2, form ε-dry), salts, hydrates and amorphous rifaximin, their use in the preparation of pharmaceutical compositions and therapeutic methods related to their use.

WO 2011/153444 describes polymorphic forms of rifaximin κ and θ and WO 2011/156897 describes polymorphic forms of rifaximin called APO-1 and APO-2.

WO 2006/094662 describes polymorphic forms δ and ε of rifaximin useful in the preparation of pharmaceutical forms for oral and topical use. Said forms are obtained by means of processes comprising hot dissolution of raw rifaximin in ethyl alcohol, then addition of water at predetermined temperatures and for predetermined time periods, then drying under vacuum.

Viscomi et al., Cryst. Eng. Comm., 2008, 10, 1074-1081 describes the process for the preparation of polymorphic forms of rifaximin and their chemical, physical and biological characteristics.

Bacchi A. et al. *New Journal of Chemistry* (2008), 32; 10; 1725-1735, describe the preparation of crystals of tetrahydrated rifaximin β with a water weight content corresponding to 8.4% (w/w), obtained by slowly evaporating water/ethanol solution of rifaximin at room temperature.

Rifaximin is a substantially water-insoluble molecule, and organic solvents are necessary to be added for increasing its solubility in aqueous solutions. Organic solvents are hardly acceptable in the preparation of substances for pharmaceutical use, and their use requires severe controls of the residual solvents in the final products.

Rifaximin water solubility can be varied within limited concentration ranges by selecting suitable polymorphic or amorphous forms. For example, WO 2005/044823 states that rifaximin polymorph α is substantially insoluble, whereas WO 2011/107970 states that an amorphous form of rifaximin obtained by means of spray-drying has a solubility of about 40 µg/ml after thirty minutes in aqueous solution, but this form is not stable and the solubility decrease over time and after two hours the solubility is about 9 µg/ml.

As described by Viscomi et al., *Cryst. Eng. Comm.*, 2008, 10, 1074-1081, rifaximin solubility in suspension the presence of solid rifaximin may vary during the time according to possible transformation processes in more stable crystalline forms. In particular, it is described that also in case of substantially amorphous rifaximin polymorphs, solubility decreases in time until it coincides with the values obtainable with the more stable crystalline forms.

Rifaximin is also a local-action antibiotic, and the in-situ bioavailability of pharmaceutical compositions providing for increased available and local rifaximin concentrations (e.g., in physiological fluids such as gastric and intestinal fluids) is useful for treating all pathologies for which an increased rifaximin concentration can provide higher therapeutic efficacy.

There is a need in the art for rifaximin formulations having increased rifaximin solubility in aqueous solutions that provide increased rifaximin concentrations that are stable with time in comparison to those obtainable by the prior art.

There is also a need to provide rifaximin pharmaceutical compositions that include amino acids for the treatment of all the diseases wherein the amino acids are efficacious. There is also a need to provide the antibiotic effect of rifaximin with the effect of the amino for the treatment of hepatic disease and debilitated disease.

There is also a need to obtain compositions providing increased rifaximin concentrations at room temperature, that may be used directly in pharmaceutical preparations, in form such as tablets or clear solutions (replacing granulates in cloudy suspensions that are not well tolerated by patients) or in compositions for vaginal or rectal use. Preferably compositions having rifaximin concentrations higher than 3 µg/ml at room temperature would be obtained therefrom.

The provision of rifaximin solutions with increased rifaximin concentration are convenient for reducing the volumes of solution needed for use in industrial processes for preparing rifaximin compositions without the addition of large volumes of organic solvents.

In particular, rifaximin concentrations having increased solubility would be useful in formulating gastroresistant compositions promoting the release of high concentrations of rifaximin in the intestine for the treatment of bowel infections.

In the prior art, rifaximin can be obtained in powder, in raw form, in polymorphic or amorphous forms.

The information concerning the crystalline characteristics of rifaximin polymorphs available in the prior art has been obtained by means of the X-ray powder diffraction techniques. The obtained powder diffractograms are the result of the contribution of several micro-crystals (or crystallites) forming the powder; the observed powder diffraction signals which are often broadened and have a non-constant intensity, even re-analyzing the same sample, since the signals can be influenced by several factors, such as, for instance, the size and morphology of the crystallites and their distribution in the sample holder. Therefore, the univocal attribution to a settled phase of a water content as well as of an exact proportion of possibly present solvates and/or hydrates by means of X-ray powder diffraction can be rather difficult.

Generally, the crystal size and structure influences some properties of the powder of an active principle. For example, Kiang Y H et al., Int. J. Pharm., 368 (2009, 76) reports that mechanical properties, such as compressibility and flowability, are related to crystal morphology (structure) and that these properties influence the preparation of finished compositions in solid form.

Vippagunta S. R. et al., *Adv. Drug. Del. Rev.* 48 (2001), 3-26, discusses the relevance of controlling the crystalline (i.e., polymorphic) forms of an active principle during the various stages of its development, because each phase change due to interconversion of the polymorphs, to solvation processes, to hydrate formation and to change of crystallinity degree can alter the bioavailability of the drug.

The correlation between solid structure (i.e., morphology) and pharmacologically useful properties, such as bioavailability, is recognized as relevant information to be considered during the drug approval process. In fact, for giving their approval to the commercialization of drugs, health authorities require suitable analytical techniques for identifying the crystalline structure of the active principle, as well as production processes of the finished product for obtaining consistent amounts of the specific polymorphic forms. For example, the European Medicines Agency that regulates the granting of marketing authorization of drugs requires that the manufacturing methods of the active ingredients are standardized and controlled in such a way that they give homogeneous and sound results in terms of polymorphism of production batches (see, CPMP/QWP/96, 2003—Note for Guidance on Chemistry of new Active Substance; CPMP/ICH/367/96—Note for guidance specifications: test procedures and acceptance criteria for new drug substances and new drug products: chemical substances; Date for coming into operation: May 2000).

Therefore, the availability of sufficiently pure, high quality crystals of a particular polymorph or solvate (including hydrates) of a suitable size is critical and quite useful for providing analytical standards that enable the identification of single polymorphs present in mixtures.

The availability of the above described analytical standards is highly relevant to the pharmaceutical arts, for example, such analytical standards are useful for the identification of the polymorphic forms present, e.g., in a mixture, and for the identification of a particular species of solvate (e.g., hydrates) characterized by the stoichiometric ratio of water to active principle. It is well known that the presence or the absence of solvent molecules (e.g., water) in specific crystallographic positions can have an influence on the position of the peaks in a powder diffractogram and, in the case of rifaximin, knowing such positions would allow a better interpretation of these diffractograms.

Also, the availability of crystals suitable for analysis via single crystal X-ray diffraction enables the identification of individual polymorphs (and solvates thereof) in complex mixtures and also the exact water content of a polymorph could be determined thanks to the information provided by such technique. In particular, the quantitative characterization of a mixture including an amorphous form of the compound is difficult because the amorphous form does not give specific signals in a diffractogram, but instead is detectable by the presence of a raised baseline in the powder diffractogram. The availability of single crystal X-ray diffraction data as an analytical standard corresponding to the polymorphs and/or solvates present in the mixture, allows the quantification of the amount of amorphous substance in a mixture.

A better understanding of the crystalline structure is also relevant for the preparation of reproducible pharmaceutical compositions. For example, production processes can be modified in order to obtain compounds with reproducible crystallinity, thus guaranteeing the presence of properties corresponding to particular crystallinity related to particular polymorphic forms.

SUMMARY OF THE INVENTION

An embodiment of the present invention is provided by compositions comprising a mixture rifaximin and amino acids, wherein amino acids and rifaximin are in a molar ratio from 1:1 to 10:1, said compositions enabling the preparation of rifaximin crystals and useful for the preparation of pharmaceutical compositions.

An embodiment of the present invention are rifaximin crystals obtained from compositions of rifaximin and amino acids dissolved in aqueous solutions, and the solution is evaporated. The obtained crystals are useful as analytical standards. A further embodiment of the present invention is the use of amino acids for increasing rifaximin concentrations in solution, in comparison to those of the state of the art.

In particular, the effect of amino acids is such that rifaximin concentrations in water of higher than 3 µg/ml at room temperature and higher than 7 µg/ml at 37° C. can be obtained.

Embodiments of the present invention also show that amino acids have a synergic effect together with organic solvents in increasing rifaximin solubility in aqueous solutions containing low percentages of organic solvents.

The use of amino acids in combination with rifaximin, according to embodiments of the present invention, provides novel compositions with rifaximin, enables the production of rifaximin crystals, e.g., suitable for analysis by single crystal x-ray diffraction, increases rifaximin concentration in aqueous solutions and provides for the preparation of pharmaceutical compositions.

Embodiments relate to pharmaceutical compositions comprising rifaximin or one of the pharmaceutically acceptable salts thereof and one or more amino acid(s), wherein the molar ratio between the amino acid(s) and rifaximin is from 1:1 to 10:1, preferably from 1:1 to 5:1, together with pharmaceutically acceptable excipients, which provide increased rifaximin solubility in aqueous solution.

In some embodiments, the pharmaceutical compositions comprise pharmaceutically acceptable ingredients that include diluting agents, binding agents, disintegrating agents, lubricating agents, release-controlling polymers or bioadhesive polymers.

Embodiments further relate to a process for preparing said pharmaceutical compositions comprising the steps
mixing rifaximin and amino acids;
adding the excipients and mixing the final mixture in, for example, a V mixer for a time from 10 to 30 minutes and
granulating the product in, for example, a roller compactor.

Embodiments further relate to the use of one or more amino acids for obtaining a pharmaceutical composition having a rifaximin concentration from 4.5 µg/ml to 60 µg/ml.

Embodiments further relate to rifaximin crystals characterized in that they are obtained by means of a process comprising:
a) dissolving rifaximin and amino acids, wherein the amino acids and rifaximin are in a molar ratio from 1:1 to 10:1 in a solution of ethanol/water, in a volumetric ratio from 1:1 to 1:10 (v/v);
b) evaporating the solution obtained in step a) at temperatures from room temperature to 40° C., in a time period from 1 to 10 days;
wherein the resulting crystals have monoclinic space group $P2_1$ and cell parameters in the ranges: a: 13.7(1)-13.8(1) Å; b: 19.7(1)-19.9(1)Å; c: 16.4(6)-16.6(6) Å; β: 92.1(1)-91.9(1) deg.

Embodiments further relate to a process for the production of rifaximin crystals, wherein the process comprises:
a) dissolving rifaximin and amino acids, wherein the amino acids and rifaximin are in a molar ratio from 1:1 to 10:1 1, in solutions of ethanol/water, in a volumetric ratio from 1:1 to 1:10 (v/v);
b) evaporating the solution obtained in step a) at temperatures from room temperature to 40° C., in a time period from 1 to 10 days.

In some embodiments, the resulting crystals are characterized by monoclinic space group $P2_1$ and cell parameters in the ranges: a: 13.7(1)-13.8(1) Å; b: 19.7(1)-19.9(1) Å; c: 16.4(6)-16.6(6) Å; β: 92.1(1)-91.9(1) deg.

Embodiments further relate to a process for the production of rifaximin crystals, wherein the process comprises:
a) dissolving rifaximin and amino acids, wherein the amino acids and rifaximin are in a molar ratio from 1:1 to 10:1, in solution of ethanol/water, in a volumetric ratio from 1:1 to 1:10 (v/v);
b) evaporating the solution obtained in step a) at temperatures from room temperature to 40° C., in a time period from 1 to 10 days, in the presence of dehydrating agents.

In some embodiments, the resulting crystals have monoclinic space group P21 and cell parameters in the ranges: a: 14.2(1)-14.5(1) Å; b: 19.7(1)-20.1(1) Å; c: 16.1(1)-16.2(1) Å; β: 108.7(1)-111.4(1) deg.

Embodiments further relate to the use of amino acids and rifaximin in a molar ratio from 1:1 to 10:1 in order to obtain rifaximin crystals. In some embodiments, the rifaximin crystals are characterized by monoclinic space group P21 and cell parameters in the ranges: a: 13.7(1)-13.8(1) Å; b: 19.7(1)-19.9(1) Å; c: 16.4(6)-16.6(6) Å; β: 92.1(1)-91.9(1) deg. In some embodiments, the rifaximin crystals are characterized by monoclinic space group P21 and cell parameters in the ranges: a: 14.2(1)-14.5(1) Å; b: 19.7(1)-20.1(1) Å; c: 16.1(1)-16.2(1) Å; β: 108.7(1)-111.4(1) deg.

The crystalline form of rifaximin in the pharmaceutical compositions according to the foregoing embodiments may be at least one selected from:
i) crystals having monoclinic space group $P2_1$ and cell parameters in the ranges: a: 13.7(1)-13.8(1) Å; b: 19.7(1)-19.9(1) Å; c: 16.4(6)-16.6(6) Å; β: 92.1(1)-91.9(1) deg.,
ii) crystals having the features of i) and having 3 or 4.5 water molecules for each rifaximin molecule,
iii) crystals having monoclinic space group P21 and cell parameters in the ranges: a: 14.2(1)-14.5(1) Å; b: 19.7(1)-20.1(1) Å; c: 16.1(1)-16.2(1) Å; β: 108.7(1)-111.4(1) deg.
iv) crystals having the features of iii) and having zero or 0.5 or 1.5 water molecules for each rifaximin molecule, or
v) rifaximin α, β, γ, δ.

In some embodiments, the compositions comprise rifaximin in the form of hydrate, solvate, polymorphous, amorphous or crystalline form or mixtures thereof.

These compositions are useful for treating and preventing inflammatory and infection diseases susceptible to rifaximin treatment.

The compositions of the invention comprise one or more amino acids wherein amino acids are aliphatic amino acids, aromatic amino acids, basic amino acids, branched amino acids, cyclic amino acids, acidic amino acids, hydroxyl or sulfur containing amino acids, amide amino acids, or mixtures thereof.

In some embodiments, the compositions of the invention comprise one or more aromatic or heterocyclic amino acids.

In one particular aspect the composition comprise a mixture of one or more aromatic or heterocyclic amino acids and branched amino acids.

In some embodiments, the compositions comprise valine, leucine, or isoleucine in a molar ratio relative to rifaximin of 10:1.

Pharmaceutical compositions can comprise rifaximin in a dosage amount of from 20 mg to 1200 mg with amino acids in a molar ratio relative to rifaximin from 1:1 to 10:1, preferably from 1:1 to 5:1. Such compositions can be administered in a dosage range of from 20 to 3000 mg per day.

Pharmaceutical compositions can be in the form of a powder, paste, granulates, tablets, capsules, pessaries, cream, ointment, suppository, suspension or solution. They can be suitable for human or animal use.

Pharmaceutical compositions can comprise amino acids and rifaximin in form of a homogenously mixed powder or in the form of "conglomerate", wherein the term conglomerate indicates rifaximin crystals and amino acids, which are generated to form a more cohesive mass between rifaximin and amino acids.

In some embodiments, conglomerates are obtained when amino acids and rifaximin, in a molar ratio from 1:1 to 10:1, preferably from 1:1 to 5:1, are solubilized in aqueous solutions in the presence of organic solvent, preferably alcohol, in a volumetric ratio from 5% to 25% at temperature between ambient temperature and boiling temperature, wherein the solvent is subsequently evaporated.

Embodiments are also directed to pharmaceutical compositions comprising rifaximin conglomerates and acceptable excipients, wherein the compositions provide increased rifaximin solubility with respect to that of the prior art.

Embodiments also relate to conglomerates of rifaximin which comprise rifaximin crystals.

The rifaximin crystals, obtained by conglomerate, are in a form of crystal and in particular in form of a single crystal suitable for X-ray diffraction and which can characterized by defined crystal parameters and water contents.

Embodiments also relate to processes for the preparation of the pharmaceutical compositions comprising one or more amino acids and rifaximin, wherein the amino acids are in a molar ratio from 1:1 to 10:1 for the preparation of solid forms as tablets, granulates, ointments, cream, suppositories and solution. The processes comprise: (a) dissolving rifaximin and one or more amino acids, wherein amino acids and rifaximin are in a molar ratio from 1:1 to 10:1, in solutions of ethanol/water, in a volumetric ratio from 1:1 to 1:10 (v/v); and (b) evaporating the solution obtained in step a). In some embodiments, evaporation of the solution takes place at temperatures from room temperature to 40° C. In some embodiments, evaporation of the solution takes place during a time period from 1 to 10 days. In some embodiments, evaporation of the solution takes place in the presence of a dehydrating agent.

Embodiments also relate to the use of pharmaceutical compositions comprising rifaximin and one or more amino acids for treatment or in the prevention of infections and disease in an animal or human in need thereof, wherein provision of rifaximin and amino acid(s) are efficacious.

In some embodiments, the composition comprising amino acids and rifaximin is provided, for example, by administering the composition, for the treatment or prevention of traveler's diarrhea, hepatic encephalopathy, infectious diarrhea, diverticular disease, as an antibacterial prophylactic prior to and post colon surgery, irritable bowel syndrome, Crohn's disease, *Clostridium difficile*-associated diarrhea, small intestinal overgrowth, traveler's diarrhea prophylaxis, dysentery, pauchitis, peptic ulcer disease, surgical prophylaxis and gastric dyspepsia. In some embodiments, the composition is provided to an animal or human in need thereof, for treatment or prevention of bowel infections, diarrhoea, irritable bowel syndrome, bacterial growth in small intestine, Crohn's disease, hepatic insufficiency, hepatic encephalopathy, enteritis and fibromyalgia.

In some embodiments, the pharmaceutical compositions comprise at least a branched amino acid beneficial in the treatment of hepatic disease such as hepatic encephalopathy and complication of cirrhosis disease.

The pharmaceutical compositions disclosed herein can provide increased local concentrations of rifaximin while providing an energetic and nourishing effect of amino acids that provides a beneficial effect for the patient.

Embodiment also relate to the use of amino acids for increasing rifaximin solubility, also in the presence of small volume of organic solvents. For example, the organic solvent can be present in an amount of from 1 to 20% (v/v).

Embodiments also relate to methods of determining the amount of rifaximin crystals in a sample of rifaximin, comprising obtaining a sample of rifaximin; carrying out a crystallographic analysis of the sample; and comparing the resulting analysis of the sample with a crystallographic analysis obtained with rifaximin crystals obtained as described herein. Such analysis may be used in the manufacture of pharmaceutical compositions for quality control, and monitoring and adjusting the amount of rifaximin in pharmaceutical composition to provide the appropriate therapeutic dose.

Embodiments also relate to methods of determining the presence of a rifaximin polymorph in a sample of rifaximin, comprising obtaining a sample of rifaximin; carrying out a crystallographic analysis of the sample; and comparing the resulting analysis of the sample with a crystallographic analysis obtained with rifaximin crystals obtained as described herein.

Other embodiments are described infra.

DETAILED DESCRIPTION OF THE INVENTION

The object of the present invention is represented by rifaximin compositions comprising one or more amino acids and rifaximin, wherein the one or more amino acids and rifaximin are in a molar ratio from 1:1 to 10:1, preferably from 1:1 to 5:1, respectively.

The compositions can be in solid form or in aqueous solutions.

Pharmaceutical compositions comprising rifaximin and one or more amino acids, wherein the amino acids are in a molar ratio to rifaximin from about 1:1 to 10:1, preferably from about 1:1 to 5:1, can provide increased rifaximin solubility on an order of magnitude from about 1.5- to 20-fold in aqueous solutions at room temperature relative to that of solutions that do not contain an amino acid. In some embodiments, such compositions can provide increased rifaximin solubility on an order of magnitude from about 1.1- to 10-fold at 37° C. relative to that of solutions that do not contain an amino acid. The increased rifaximin solubility can vary according to the chosen amino acid.

The increase in rifaximin solubility in the presence of amino acids is observed when the compositions comprise rifaximin in the form of raw rifaximin, amorphous rifaximin, a rifaximin polymorph, or mixtures thereof.

When amino acids are in solution with low volumetric percentages of organic solvents, in particular from 1% to 25% (V/V), a synergic effect resulting from the presence of amino acids and organic solvents on the increasing of rifaximin solubility is observed and the solubility increases up to thousand time reaching concentrations higher than 30 mg/ml.

The synergistic effect of the one or more amino acids in combination with organic solvents on aqueous rifaximin solubility is also advantageous for the manufacturing process of the pharmaceutical compositions described herein. For example, the use of organic solvent during the manufacturing process can be avoided or reduced. In addition, the synergistic effect provided by amino acids in the presence of small volumes of organic solvent can provide solutions with higher concentrations of rifaximin, which can be used to form conglomerates of rifaximin and amino acids as described herein.

The one or more amino acids present in rifaximin compositions of the present invention can be an aliphatic amino acid, such as, for example, glycine or alanine; a branched amino acid, such as, for example, valine, leucine or isoleucine; a hydroxyl or sulfur containing amino acid, such as, for example, cysteine, threonine or methionine; a cyclic amino acid, such as, for example, proline; a heterocyclic amino acid, such as, for example, proline or histidine; an aromatic amino acid, such as, for example, phenylalanine, tyrosine or tryptophan; a basic amino acid, such as, for example, histidine, lysine or arginine; an acidic amino acid, such as, for example, aspartic acid or glutamic acid; an amide amino acid such as, for example, asparagine or glutamine; or mixtures thereof.

The use of different amino acids leads to different rifaximin concentrations, thus, it is possible to modulate rifaximin solubility in an aqueous solution, for use directly or for use in manufacturing a pharmaceutical composition, including solid compositions, for different diseases.

It has been found that aromatic amino acids or amino acids comprising a heterocyclic ring provide higher solubility of rifaximin in aqueous solutions.

In particular it has been found that the presence of tryptophan and/or histidine provides increased solubility of rifaximin.

Compositions of the present invention comprise rifaximin in the form of a hydrate, a solvate, a polymorphous form, amorphous form, or mixtures thereof, and one or more amino acids, wherein the one or more amino acids and rifaximin are present in a molar ratio preferably from about 1:1 and 10:1, more preferably from about 1:1 and 5:1. Such compositions can be formulated with one or more pharmaceutically acceptable excipients for the preparation of pharmaceutical compositions in solid or liquid form.

In humans and animals, amino acids have important roles as metabolic intermediates. When administered to humans, the amino acids either are used to synthesize proteins or other biomolecules, or they are oxidized to urea and carbon dioxide as a source of energy.

Amino acids also have an energetic and nourishing effect, therefore, the use of amino acids in pharmaceutical compositions comprising rifaximin for the treatment of all pathologies that are susceptible to treatment with rifaximin with related debilitative diseases can have a beneficial effect on a patient in need thereof.

Compositions comprising one or more amino acids are described herein. In a preferred embodiment, compositions comprising aromatic amino acid and branched amino acids such as leucine, isoleucine and valine are useful for increasing solubility of rifaximin as well as for providing a beneficial effect in the treatment of hepatic encephalopathy. These compositions have the advantage of providing a higher available concentration of rifaximin relative to that of the prior art in the treatment of hepatic encephalopathy.

The compositions comprising rifaximin and amino acids of the invention also have the advantage of providing for an increased amount of soluble rifaximin and therefore a higher concentration of rifaximin available at the site of action, thus allowing better efficacy and/or total amount of drug administered, and depending on the form, locally or more systemically. In particular, the addition of amino acids to rifaximin in gastroresistant and/or controlled release compositions allows the release of higher rifaximin concentrations in the intestinal tract where an infection is localized.

Compositions of the present invention can also comprise rifaximin and one or more amino acids in the form of conglomerates of rifaximin and amino acids, wherein the term "conglomerate" refers to a solid material obtained by drying an aqueous solution of rifaximin and amino acids. The conglomerates of the present invention are characterized by the presence of crystals of rifaximin and crystals of one or more amino acids wherein the rifaximin crystals have suitable size and quality to be analyzed by single crystal x-ray diffraction. Preferably, one or more crystals of rifaximin in the conglomerates are characterized by the dimensions from 0.1 mm to 0.3 mm×from 0.1 mm to 0.3 mm×from 0.1 mm to 0.3 mm. The conglomerates of the invention comprising amino acids and rifaximin can be obtained by drying aqueous solutions having a molar ratio of amino acids to rifaximin ranging from 1:1 to 10:1. In some embodiments, the aqueous solutions are dried by evaporation. Pharmaceutical excipients can be added to these conglomerates for the preparation of a desired form and further, to provide single rifaximin crystals, characterized by forms of pure crystal.

The rifaximin crystals, so obtained, are useful as analytical standards.

The amino acids-rifaximin compositions can also comprise conglomerates of rifaximin with acceptable pharmaceutical excipients. The preparation of such pharmaceutical compositions of the invention comprise the steps of obtaining a conglomerate of rifaximin and one or more amino acids and the step of combining the conglomerate with pharmaceutically acceptable excipients.

Compositions comprising rifaximin and one or more amino acids, or conglomerates containing the same, can be in the form of granules which may optionally be coated with one or more controlled release agents. The granules, together with extragranular excipients, can be used for the preparation of pharmaceutical compositions. The term "acceptable ingredients" includes pharmaceutically acceptable materials, compositions or vehicles, such as liquid or solid fillers, diluents, excipients, solvents or encapsulating material suitable for human or animal use.

Diluting agents, disintegrating agents, lubricating agents, polymers for conferring gastroresistance or controlled release are included, for example, among the excipients useful in the preparation of pharmaceutical compositions.

Exemplary diluting agents useful in the preparation of pharmaceutical compositions described herein can include, but not be limited to, at least one selected from the group consisting cellulose, microcrystalline cellulose, calcium phosphate, starch, kaolin, dehydrated calcium sulphate, calcium carbonate, lactose, saccharose, glucose, sorbitol and mannitol Exemplary binding agents useful in the preparation of pharmaceutical compositions described herein can include, but not be limited to, at least one selected from the group consisting of cellulose, cellulose derivatives, carboxy methyl cellulose, microcrystalline cellulose, hydroxy propyl cellulose, hydroxy ethyl cellulose, hydroxy propyl-methyl cellulose, starches, potato starch, maize starch, partially gelatinized starch, gums, synthetic gum, natural gums, polyvinyl pyrrolidone, polyethylene glycol, gelatin, polyols, propylene glycol, alginates and sugars.

Exemplary disintegrating agents useful in the preparation of pharmaceutical compositions described herein can include, but not be limited to, at least one selected from the group consisting of sodium carboxy methyl cellulose (also called carmelose sodium), cross-linked sodium carboxy methyl cellulose (also called croscarmelose sodium), polyvinyl pyrrolidone (also called povidone), cross-linked polyvinyl pyrrolidone (also called crospovidone), starch, pregelatinized starch, and silica. Exemplary lubricating agents useful in the preparation of pharmaceutical compositions described herein can include, but not be limited to, at least one selected from the group consisting of silica, magnesium stearate, calcium stearate, sodium stearyl fumarate, hydrogenated vegetable oils, mineral oils, polyethylene glycols, sodium lauryl sulphate, glycerides, sodium benzoate, glyceryl dibehenate and glycerol stearate.

The polymers suitable for obtaining controlled release can have a synthetic or natural origin. Exemplary polymers suitable for the preparation of the pharmaceutical compositions described herein can include, but not be limited to, at least one selected from the group consisting of copolymers of acrylic acid, such as the copolymer methacrylic acid-ethyl acrylate 1:1, copolymers of methacrylic acid with an acrylic or methacrylic ester such as the copolymer methacrylic acid-ethyl acrylate 1:1 and the copolymer methacrylic acid-methyl methacrylate 1:2, polyvinyl acetate phthalate, hydroxy propyl methyl cellulose phthalate, cellulose acetate phthalate, commercially available products, for instance with the trademarks Kollicoat®, Eudragit®, Aquateric®, Aqoat®; natural polymers like shellac, commercially available with the trademark Aquagold® (shellac 25%) and ethyl cellulose.

The pharmaceutical compositions described herein can also have bioadhesive properties in order to adhere to intestinal mucosa. Examples of polymers, oligomers or their mixtures which can confer bioadhesive properties can include at least, but not be limited to, one selected from the group consisting of: pectins, zeins, casein, gelatin, albumin, collagen, kitosan, oligosaccharides and polysaccharides such as, for instance, cellulose, dextran, polysaccharides from tamarind seeds, xanthan gum, arabic gum, hyaluronic acid, alginic acid and sodium alginate.

When the bioadhesive polymer is a synthetic polymer, the polymer can be, but not limited to, at least one selected from the group consisting of polyamides, polycarbonates, polyalkylenes, polyalkylene glycols, polyalkylene oxides, polyalkylene terephthalates, polyvinyl alcohols, polyvinyl ethers, polyvinyl esters, polyvinyl pyrrolidone, polysiloxanes, polyurethanes, polystyrenes, polymers of acrylic acid and methacrylic esters, copolymers of methacrylic acid-ethyl acrylate, polylactides, barbituric polyacids, polyanhydrides and polyorthoesters.

Further useful polymers include, for example, methyl cellulose, ethyl cellulose, hydroxy propyl cellulose, hydroxy butyl methyl cellulose, cellulose acetate, cellulose propionate, cellulose acetate butyrate, cellulose acetate phthalate, carboxy methyl cellulose, cellulose triacetate, cellulose sulfate sodium salt, polymethyl methacrylate, poly isobutyl acrylate, poly octadecyl acrylate, polypropylene, polyethylene glycol, polyethylene oxide, polyethylene terephthalate, polyvinyl acetate, polyvinyl chloride, polystyrene, polyvinyl pyrrolidone, polyvinyl phenol and mixtures thereof.

Another group of polymers useful in the obtainment of bioadhesivity are polymers having a branch with at least one bonded hydrophobic group, wherein hydrophobic groups generally are non-polar groups. Examples of said hydrophobic groups can include at least, but not be limited to, one selected from the group consisting of alkyls, alkenyls and alkyl groups. Preferably, hydrophobic groups are chosen to increase polymers bioadhesivity. Other polymers are characterized by hydrophobic branches with at least one hydrophilic group, such as carboxylic acids, sulphonic acids and phosphonic acids, neutral and positively charged amines, amides and imines, wherein the hydrophilic groups are such to increase the polymer bioadhesivity.

Pharmaceutical compositions comprising rifaximin and amino acids can optionally comprise also edulcorating agents, coloring agents, anti-oxidizing agents, buffering agents and flavoring agents.

Exemplary edulcorating/sweetening agents useful in the preparation of pharmaceutical compositions described herein can include, but not be limited to, at least one selected from the group consisting of potassium acesulfame, sorbitol, mannitol, isomalt, maltitol, lactitol, xylitol, aspartame, cyclamic acid, cyclamate salts, lactose, sucralose, saccharine and saccharine salts.

When the amino acids-rifaximin compositions are administered as pharmaceuticals to humans and animals, they can be given without other excipients, or as a pharmaceutical composition containing, for example, from 0.1 to 90% of active ingredient in combination with one or more pharmaceutically acceptable excipients, such as a carrier.

The pharmaceutical compositions comprising rifaximin and one or more amino acids, together with pharmaceutically acceptable excipients, can be in the form of granulates, tablets, capsules, creams, ointments, suppository, suspensions or solutions of rifaximin suitable for human and/or animal administration.

The pharmaceutical compositions comprising rifaximin and one or more amino acids can include rifaximin in an amount from 20 to 1200 mg, for example, 30, 40, 50, 100, 200, 400, 600, 800 and 1000, preferably from 100 to 600 mg. Such compositions are useful in the prevention and treatment of, for example, traveler's diarrhea, hepatic insufficiency, hepatic encephalopathy, infectious diarrhea, diverticular disease, an antibacterial prophylactic prior and post colon surgery, irritable bowel syndrome, Crohn's disease, *Clostridium difficile*-associated diarrhea, small intestinal overgrowth, traveler's diarrhea prophylaxis, dysentery, pauchitis, peptic ulcer disease, surgical prophylaxis, gastric dyspepsia enteritis, fibromyalgia, vaginal infections and as an antibacterial prophylactic prior to and/or post colon surgery.

Actual dosage levels and time course of administration of the active ingredients in the pharmaceutical compositions may be varied so as to obtain an amount of the active ingredient which is effective to achieve the desired therapeutic response for a particular subject, composition, and mode of administration, without being toxic to the subject. An exemplary dose range is from 20 to 3000 mg per day. Other doses include, for example, 600 mg/day, 1100 mg/day and 1650 mg/day. Other exemplary doses include, for example, 1000 mg/day, 1500 mg/day, from 500 mg to about 1800 mg/day or any value in-between.

The amino acids amount is typically in a molar ratio from 1 to 10 with respect to the rifaximin, preferably in a molar ratio from 1 to 5. In embodiments in which the amino acids are branched amino acids, the amount of amino acid present in the composition is preferably in a molar ratio of from 1 to 10 with respect to the rifaximin.

The pharmaceutical compositions can be formed by various methods known in the art, such as, for example, granulation, direct compression or double compression. In a preferred embodiment, the processes for making a pharmaceutical composition, wherein amino acids are in a molar ratio from 10:1 to 5:1 with respect to rifaximin, comprise the steps of mixing rifaximin and one or more amino acids to obtain a homogeneous mixture and adding excipients for preparation of the composition in solid or liquid form for oral administration. Suitable forms include, for example tablets, powder, granules, pastes and capsules. Suitable modes of administration include parenteral administration, for example, by subcutaneous, intramuscular or intravenous injections of, for example, a sterile solution or suspension; topical application, for example, as a cream, ointment or spray applied to the skin; intravaginally or intrarectally, for example, as a pessary, cream, a foam; or an aerosol.

Conglomerates of rifaximin and amino acids allow for stable storage of rifaximin without any rifaximin transformation as well as being useful for obtaining single crystals of rifaximin. the preparation of rifaximin crystals in the conglomerates comprises mixing rifaximin and one or more amino acids in aqueous solution and complete evaporation of solvent at room temperature or at temperatures between room temperature and 100° C. The drying step can take place in the presence or absence of dehydrating agents and can occur at ambient pressure or under vacuum. The resulting crystals are analyzed and characterized by having high purity with sizes that are suitable for structure characterization via single crystal X-ray diffraction. The crystals are parallel-piped or cubed, and preferably their dimension are from 0.1 mm to 0.3 mm×from 0.1 mm to 0.3 mm×from 0.1 mm to 0.3 mm.

The compositions of rifaximin and amino acids allow to obtain rifaximin crystals. These latter are obtained when the compositions of rifaximin and amino acids contain amino acids and rifaximin in a molar ratio from 1:1 to 10:1, preferably from 1:1 to 5:1, wherein the amino acids and rifaximin are dissolved in aqueous solutions comprising alcohols in a volumetric water/alcohol ratio from 1:1 to 10:1 (v/v), preferably about 5:1 (v/v), wherein the rifaximin concentration in solution is higher than 15 mg/ml.

In some embodiments, rifaximin crystals are obtained by means of a process comprising a evaporation of the aforesaid solutions of rifaximin and amino acids at room temperature or at temperatures from room temperature to 100° C., followed by a drying step, which be in the presence or absence of dehydrating agents. The resulting crystals are characterized by having high purity and by being a sufficient size for being analyzed by means of single crystal X-ray diffraction.

The rifaximin comprised in the compositions for formation of rifaximin crystals can be raw rifaximin, amorphous rifaximin, pure rifaximin polymorphs, and solvates or mixtures thereof. The compositions may include the presence of single amino acids or mixtures thereof.

Rifaximin crystals obtained as described herein have been characterized by means of the X-ray diffraction technique, which provide, for example, information about cell parameters and structural details (atomic coordinates, connectivity, distances and bond angles). The rifaximin crystals analyzed by X-ray diffraction were characterized as having cell parameters a, b, c, and $\alpha$, $\beta$ and $\gamma$ within the ranges reported in Table 1.

TABLE 1

| Values of cell parameters | |
|---|---|
| a/Å | 13.7(1)-13.8(1) |
| b/Å | 19.7(1)-19.9(1) |
| c/Å | 16.4(6)-16.6(6) |
| α/deg | 90 |
| β/deg | 92.1(1)-91.9(1) |
| γ/deg | 90 |

In particular, rifaximin crystals obtained by the methods described herein are characterized by the following cell parameters:
crystal 1: a: 13.7960(8) Å; b: 19.944(4) Å; c: 16.607(6) Å; β: 92.180(1) deg; α and γ: 90 deg;
crystal 2: a: 13.753(8) Å; b: 19.749(4) Å; c: 16.378(6) Å; β: 91.972(1) deg; α and γ: 90 deg.

Knowledge of cell parameters and structural details allows the calculation of the theoretical diffractogram, which is then compared to the experimental diffractograms obtained from the powder samples of rifaximin.

This comparison shows that the crystals described in Table 1, identified as crystals "1" and "2" are crystals of rifaximin β. Crystal 1 contains stoichiometrically 3 water molecules for each rifaximin molecule, and is called rifaximin $\beta_{3.0}$ (where the subscript indicates the number of water molecules for each rifaximin molecule); crystal 2 contains stoichiometrically 4.5 water molecules for each rifaximin molecule, and is called rifaximin $\beta_{4.5}$.

Other rifaximin crystals have been obtained by means of drying of solutions comprising rifaximin and one or more amino acids, or by means of direct drying (e.g. in the presence of $P_2O_5$) of crystals of rifaximin β, wherein the size of the formed crystals is large enough to be analyzed by single crystal X-ray diffraction.

Such rifaximin crystals, analyzed by means of single crystal X-ray diffraction, are characterized as having cell parameters a, b c and α, β and γ comprised in the ranges reported in Table 2.

TABLE 2

| Values of cell parameters | |
|---|---|
| a/Å | 14.2(1)-14.5(1) |
| b/Å | 19.7(1)-20.1(1) |
| c/Å | 16.1(1)-16.2(1) |
| α/deg | 90 |
| β/deg | 108.7(1)-111.4(1) |
| γ/deg | 90 |

In particular, rifaximin crystals have been found which are characterized by the following cell parameters:
crystal 3: a: 14.232(4) Å; b: 19.822(4) Å; c: 16.164(4) Å; β: 108.74(3) deg; α and γ: 90 deg;
crystal 4: a: 14.579(4) Å; b: 20.232(4) Å; c: 16.329(4) Å; β: 111.21(3) deg; α and γ: 90 deg;
crystal 5: a: 14.492(4) Å; b: 20.098(4) Å; c: 16.215(4) Å; β: 111.21(3); α and γ: 90 deg.

Comparison of the theoretical diffractogram of the crystals with the experimental diffractogram obtained from the powder samples of rifaximin indicate that the crystals previously described in Table 2 (e.g. crystal 3, crystal 4 and crystal 5) are crystals of rifaximin α.

In particular, crystal 3 does not contain any water molecule, and is called α0; crystal 4 contains stoichiometrically 0.5 water molecules for each rifaximin molecule and is called rifaximin $α_{0.5}$; crystal 5 contains stoichiometrically 1.5 water molecules for each rifaximin molecule and is called rifaximin $α_{1.5}$.

Rifaximin single crystals as described herein can be obtained when the rifaximin and one or more amino acids are mixed in aqueous solution. The rifaximin in solution can be raw rifaximin, amorphous rifaximin, rifaximin polymorph or mixtures thereof.

Rifaximin crystals can also be obtained from conglomerates comprising rifaximin and one or more amino acids. Such crystals can be crystals of rifaximin β and, such as, for example, crystals of rifaximin β with 3 water molecules for each rifaximin molecule ("rifaximin $β_{3.0}$"); or a crystal of rifaximin β with 4.5 water molecules for each rifaximin molecule ("rifaximin $β_{4.5}$").

Other rifaximin crystals can be obtained by means of drying of solutions comprising rifaximin and one or more amino acids, or by means of direct drying (e.g. $P_2O_5$) of crystals of rifaximin β, wherein the size of these crystals is large enough to be analyzed by single crystal X-ray diffraction.

On the basis of cell parameters and structural details it is possible to calculate the theoretical diffractogram which is then compared to the experimental one obtained from the powders. As described herein, obtained crystals can include crystals of rifaximin α. In some embodiments, the crystals of rifaximin α do not contain any water molecule ("$α_0$"). In some embodiments, the crystals of rifaximin α have 0.5 water molecules for each rifaximin molecule ("$α_{0.5}$"). In some embodiments, the crystals of rifaximin α contain 1.5 water molecules for each rifaximin molecule ("$α_{1.5}$").

The crystalline structures of rifaximin $β_{4.5}$, $β_3$, $α_{1.5}$ and $α_{0.5}$ are hydrates that have the characteristic of containing at least one water molecule for each dimeric unit, characterized in that the water interacts by means of a hydrogen bond with the amide nitrogen at position 14; this water molecule enters the ansa chain of the rifaximin structure.

In the microcrystalline powders described in the literature, the diffraction profile is given by the superimposition of the diffraction profiles of single crystals constituting the powder, each of which is characterized by a different content of crystallization water. Therefore, obtaining single rifaximin crystals with a suitable size for structural analysis (e.g. by means of single crystal X-ray diffraction) can provide useful structural parameters, from which it is then possible to calculate rifaximin diffractograms corresponding to different contents of crystallization water.

Single rifaximin crystals thereby obtained can be used as analytical standards in crystallographic analysis for the quantitative and qualitative determination of rifaximin mixtures, even complex ones, wherein crystals characterized by different water contents and by cell parameters within the ranges reported in Tables 1 and 2 are present in variable proportion.

The number and position of water molecules within individual rifaximin crystals influence the parameters of the unit cell as well as the position of the peaks in the X-ray powder diffractogram. The obtained crystals allow determination of the presence of a polymorphic form, even in complex mixtures.

The parameters characterizing the rifaximin crystals described in Examples 2, 4, 6 and 8 have been obtained in the laboratory by means of an Oxford Diffraction X'calibur diffractometer with MoKα radiation (λ=0.71073 Å) or by means of an XRD1 line at the Elettra Synchrotron in Trieste.

Rifaximin single crystals are useful in quantitatively and qualitatively determining the presence of such polymorphic forms in complex rifaximin mixtures, in production batches and in finished pharmaceutical compositions comprising rifaximin, and they can also be useful in determining the amorphous amount in a powder mixture.

In addition to providing methods of obtaining single rifaximin crystals, the use of amino acids is also advantageous in industrial processes for the preparation of rifaximin pharmaceutical compositions. For example, the presence of one or more amino acids can increase the solubility of rifaximin in an aqueous solution, thereby allowing avoidance or reduction of the volume of organic solvents to be used. This has relevance for products for human or animal use as the amount of residual organic solvents in the product can be reduced.

Avoidance or reduction of use of organic solvent can also contribute to the safety of the industrial process to make pharmaceutical compositions comprising rifaximin. For example, lower quantities of organic solvents can increase the flash point of an aqueous solution of rifaximin.

Rifaximin compositions in the presence of one or more amino acids, wherein the molar ratio of amino acid to rifaximin is from 1:1 and 10:1, preferably from 1:1 and 5:1, can provide an increase of rifaximin solubility on an order of magnitude of from 1.5- to 20-fold in aqueous solutions at room temperature. In some embodiments, the compositions comprising rifaximin and one or more amino acids can provide an increase of rifaximin solubility on an order of magnitude of from about 1.1- to 10-fold at 37° C., depending upon the selected amino acid(s).

The increase in rifaximin solubility in the presence of one or more amino acids is observed with raw rifaximin, amorphous rifaximin, rifaximin pure polymorphs or their mixtures in the presence of single amino acids or their mixtures. It has also been observed that the presence of amino acids can have a synergic effect on rifaximin solubility in aqueous solutions in which low percentages of organic solvents are present. For example, the effect is observed in aqueous solutions in which organic solvents are present in an amount equal to or less than about 20% (v/v).

As shown in Example 11, the solubility of rifaximin in an ethanol/water solution 1:4 (v/v) containing amino acids in a molar ratio relative to rifaximin from 1:3 and 1:5 is 48 μg/mL. As shown in Examples 2, 4, 6 and 8 and 10, rifaximin is solubilized at concentrations which are nearly thousand times higher, thus reaching concentrations higher than 30 mg/ml in solution at elevated temperatures, e.g., 100° C. The possible use of water/ethanol solutions with a low ethanol content in the production process of crystalline rifaximin represents an advantage from the point of view of the process safety. Such solutions have a higher point of inflammability, also called "flash point", defined as the minimum temperature at which, at room pressure, a liquid produces vapors in such an amount that, together with air, they form a mixture which can flare up or explode. Therefore, the higher the flash point, the safer the process.

In the case of 20% ethanol solutions (v/v) in water, as in Example 2, the flash point is 36° C., whereas for 70% ethanol solutions, like those described in the known art for rifaximin crystallization, the flash point decreases to 21° C.

Moreover, another advantage is that in solutions having a low ethanol content, rifaximin crystallization can be coupled to crystallization of amino acids that may be present in the solution, thus allowing the obtainment of both crystal forms as a mixture in the solid state using a single step.

Different amino acids lead to different available rifaximin concentrations, thus allowing the modulation of rifaximin solubility.

The Examples describe the preparation of solid compositions comprising different amino acids in various molar ratios with respect to rifaximin, in form of granules for ready suspension and/or tablets. In some embodiments, preparations of solid compositions are provided, wherein the compositions comprise rifaximin and tryptophan, serine and histidine in molar ratios from 10 to 1 with respect to the rifaximin.

Embodiments are also directed to compositions in the form of granules for ready suspension or for tablet preparations, wherein said granules can include or are coated with agents for controlling release. Exemplary agents for controlled release are described supra.

The composition can also be in the form of tablets that are coated with a coating or film to provide controlled release.

Embodiments also relate to methods of increasing the solubility of rifaximin in a composition, wherein one or more amino acid are comprised in the composition. In some embodiments, a synergic effect on rifaximin solubility is observed when the one or more amino acids are provided in the composition in the presence of low volumes of organic solvents.

The Examples described herein also demonstrate that the effect of amino acids on increased rifaximin solubility is even higher than the effect given under fasting and fed conditions Example 1 describes the preparation of solid compositions of rifaximin and amino acids wherein different amino acids, such as tryptophan, serine and histidine, are mixed in molar ratios from 1:1 to 5:1 relative to rifaximin (amorphous form or polymorph α).

Example 2 describes the preparation of rifaximin crystals by means of a process comprising the solubilization of composition A of Example 1 in a solution of ethanol/water 1:4 (v/v), wherein rifaximin reaches a concentration in solution corresponding to 40 mg/ml at elevated temperatures, e.g. 100° C. A solid mass, which can be defined as a conglomerate, or an assembly of distinguishable and separable crystals of rifaximin and amino acids, is obtained by slow evaporation of the solution.

Example 3 describes the structural characterization, by means of X-ray diffraction from a conventional source or from a synchrotron, of rifaximin crystals obtained from Example 2. The structural resolution allows to establish that the analyzed crystals are crystals of rifaximin β, characterized in that they have 3 and 4.5 water molecules per rifaximin molecule.

Examples 4 and 5 describe the preparation and characterization of rifaximin crystals by single x-ray diffraction obtained by solubilization of the composition B of Example 1 in a solution of ethanol/water 1:4 (v/v), wherein rifaximin reaches a concentration corresponding to 40 mg/ml at elevated temperatures, e.g., 100° C. Examples 6 and 7 describe the preparation and characterization of rifaximin crystals obtained from composition C of Example 1.

Examples 8 and 9 describe the preparation and characterization of rifaximin crystals obtained from composition D of Example 1.

Example 10 describes the preparation of crystals of rifaximin α obtained by transforming the rifaximin crystal obtained in Example 2 in the presence of dehydrating agents. The same result can be obtained by drying the solid mass comprising crystals of rifaximin and amino acids obtained according to Examples 2, 4, 6, and 8 in the presence of dehydrating agents or under vacuum and at temperatures between room temperature and 40° C.

Comparative Example 11 demonstrates that, in the absence of amino acids, rifaximin in a solution of ethanol/water 1:4 (v/v) reaches a maximum concentration of 48 µg/ml.

Example 12 shows a comparison of rifaximin solubility in aqueous solutions with or without amino acids at various temperatures. Rifaximin solubility in aqueous solutions turns out to be about 3 µg/ml at room temperature and about 7 µg/ml at 37° C., whereas in the presence of amino acids its solubility is higher than 30 µg/mL in both cases. These results disclose preparations of pharmaceutical compositions wherein rifaximin is more available.

Example 13 describes the solubility of the solid mass, defined as a conglomerate of amino acids and crystals of rifaximin, prepared according to Example 2, which in buffer solution at pH 6.8 reaches a rifaximin concentration corresponding to about 30 µg/ml.

These examples demonstrate that the compositions containing rifaximin and one or more amino acids can lead to higher concentration of rifaximin in water or aqueous solutions compared to solutions wherein amino acids are not present.

Examples 14 and 15 are comparison studies or rifaximin solubility. These examples provide rifaximin solubility values in water and buffers at room temperature and at 37° C., in the absence of organic solvents and amino acids.

Example 14 describes rifaximin solubility in water and in buffers at pH 4, pH 7 and pH 10. These studies demonstrate that rifaximin is substantially insoluble in water, in particular at those pH values which are similar to the physiologic conditions.

Example 15 describes rifaximin solubility obtained by means of the dissolution test of coated tablets and tablets comprising rifaximin gastroresistant granules, in solutions simulating intestinal fluids before meals (FaSSIF solutions) and after meals (FeSSIF solutions).

Coated rifaximin tablets (NORMIX®) show rifaximin solubility values in FaSSIF solutions of about 8 µg/ml after 360 minutes, whereas in FeSSIF solutions rifaximin concentration is about 11 µg/ml after 360 minutes.

The tablets comprising gastroresistant granules in rifaximin show a rifaximin solubility in FaSSIF solutions of about 13 µg/ml after 360 minutes, whereas in FeSSIF solutions rifaximin concentration is about 20 µg/ml after 360 minutes.

The examples of the invention show that the effect exerted by amino acids on increasing rifaximin solubility exceeds rifaximin solubility of rifaximin compositions prepared in the absence of amino acids in intestinal fluids. The addition of amino acids to gastroresistant and non gastroresistant compositions may therefore provide higher levels of bioavailable rifaximin concentrations, in particular after meals.

Example 1

Preparation of Solid Compositions Comprising Rifaximin and Amino Acids

A rifaximin amount corresponding to 200 mg was mixed in a V-mixer together with respective amounts of amino acid (AA) as reported in Table 3.

TABLE 3

| Composition | Amino acid (AA) | Rifaximin form | Molar ratio AA:rifaximin |
|---|---|---|---|
| A | Tryptophan | Rifaximin α | 4:1 |
| B | Serine | Rifaximin α | 3:1 |
| C | Histidine | Rifaximin α | 4:1 |
| D | Histidine | Amorphous Rifaximin | 4:1 |

The obtained mixture can be stored at room temperature without any particular further precaution beside those taken for storing rifaximin or amino acids alone.

Example 2

Preparation of Crystals of Rifaximin β Starting from the Composition A of Example 1

5 ml of a solution formed by ethanol/water in volumetric ratio 1:4 (v/v) were added to composition A of Example 1. The mixture was then heated at 100° C. until reaching complete dissolution and left for complete solvent evaporation at room temperature for 4 days. Formation of rifaximin conglomerates characterized by the contemporary presence of rifaximin crystals and tryptophan crystals were obtained after solvent evaporation.

Example 3

Analysis of Crystals of Rifaximin β3.0 and β4.5 Obtained in Example 2

Rifaximin crystals obtained in Example 2 were separated from amino acids and measured by X-ray diffraction using:

a) An X'calibur diffractometer by Oxford Diffraction, provided with a CCD area detector which uses MoKα radiation (λ=0.71073 Å) and a graphite monochromator; data were collected at room temperature. The structures were solved by direct methods using the SHELX97 program (Sheldrick, 2008) implemented in the WinGX package (Farrugia, 1999);

b) synchrotron ELETTRA (Trieste) at the XRD1 beam line at room temperature and at 295 K, using the cooling system MARSCH 300.

The structures were solved using the SHELX97 program (Sheldrick, 2008) implemented in the WinGX package (Farrugia, 1999). Table 4 reports the crystallographic parameters relating to the analyzed rifaximin crystals.

TABLE 4

| | Crystallographic parameters | Crystallographic parameters |
|---|---|---|
| Chemical formula | $C_{43}H_{57}N_3O_{14}$ | $C_{43}H_{60}N_3O_{15.5}$ |
| $H_2O$ molecules for each rifaximin molecule | 3.0 | 4.5 |
| MW | 839.93 | 866.95 |
| Temperature/K | 295 | 295 |
| λ(Å) | 0.71073 | 1 |
| Crystalline system | monoclinic | monoclinic |
| Space group | $P2_1$ | $P2_1$ |
| a/Å | 13.7960(8) | 13.753(8) |
| b/Å | 19.944(4) | 19.749(4) |
| c/Å | 16.607(6) | 16.378(6) |
| β/deg | 92.180(1) | 91.972(1) |
| V/Å$^3$ | 4566.1 | 4445.8(6) |
| Z | 4 | 4 |
| $D_c$/Mg m$^{-3}$ | 1.222 | 1.295 |

Based on the known cell parameters and structural details, the crystals (Example 2) were determined to be crystals of rifaximin β, called rifaximin β$_{3.0}$ and rifaximin β$_{4.5}$.

Example 4

Preparation of Rifaximin Crystals Starting from the Composition B of Example 1

5 ml of a solution formed by ethanol/water in a volumetric ratio 1:4 (v/v) were added to composition B of Example 1. The mixture was then heated at 100° C. until reaching complete dissolution and left for complete solvent evaporation at room temperature for 4 days. Formation of rifaximin crystals and serine crystals was obtained after solvent evaporation.

Example 5

Analysis of Rifaximin Crystals Obtained in Example 4

Rifaximin crystals obtained in Example 4 were separated from amino acids crystals. Cell parameters were determined at room temperature by means of an X'calibur diffractometer by Oxford Diffraction using the MoKα radiation (λ=0.71073 Å).

Table 5 reports crystallographic parameters relating to the analyzed rifaximin crystal.

TABLE 5

| | Crystallographic parameters |
|---|---|
| Temperature/K | 295 |
| Morphology | Orange prism |
| Crystalline system | monoclinic |
| Space group | $P2_1$ |
| a/Å | 13.86(1) |
| b/Å | 19.90(1) |
| c/Å | 16.69(1) |
| β/deg | 91.85(1) |

Based on the known cell parameters, the analyzed crystal was determined to be a crystal of rifaximin β.

Example 6

Preparation of Rifaximin Crystals Starting from the Composition C of Example 1

5 ml of a solution formed by ethanol/water in a volumetric ratio 1:4 (v/v) were added to composition C of Example 1.

The solution was then heated at 100° C. until reaching complete dissolution and left at room temperature for 4 days for evaporation of the solvent. Formation of rifaximin crystals and histidine crystals were obtained after solvent evaporation.

Example 7

Analysis of Rifaximin Crystals Obtained in Example 6

Rifaximin crystals obtained in Example 6 were separated from amino acids crystals. Cell parameters were determined at room temperature by means of an X'calibur diffractometer by Oxford Diffraction using the MoKα radiation ($\lambda=0.71073$ Å).

Table 6 reports crystallographic parameters relating to the analyzed rifaximin crystal.

TABLE 6

|  | Crystallographic parameters |
| --- | --- |
| Temperature/K | 295 |
| Morphology | Orange prism |
| Crystalline system | monoclinic |
| Space group | $P2_1$ |
| a/Å | 13.75(1) |
| b/Å | 19.76(1) |
| c/Å | 16.35(1) |
| β/deg | 92.09(1) |

Based on known cell parameters, the analyzed crystal was determined to be a crystal of rifaximin β.

Example 8

Preparation of Rifaximin Crystals Starting from the Composition D of Example 1

5 ml of a solution formed by ethanol/water in a volumetric ratio 1:4 (v/v) were added to composition D of Example 1. The solution was then heated at 100° C. until reaching complete dissolution and left at room temperature for 4 days for evaporation of the solvent. Formation of rifaximin crystals and histidine crystals were obtained after solvent evaporation.

Example 9

Analysis of Rifaximin Crystals Obtained in Example 8

Rifaximin crystals obtained in Example 8 were separated from amino acids crystals. Cell parameters were determined at room temperature by means of an X'calibur diffractometer by Oxford Diffraction using the MoKα radiation ($\lambda=0.71073$ Å).

Table 7 reports crystallographic parameters relating to the analyzed rifaximin crystal.

TABLE 7

|  | Crystallographic parameters |
| --- | --- |
| Temperature/K | 295 |
| Morphology | Orange prism |
| Crystalline system | monoclinic |
| Space group | $P2_1$ |
| a/Å | 13.78(1) |
| b/Å | 19.74(1) |
| c/Å | 16.38(1) |
| β/deg | 92.12(1) |

Based on these cell parameters, the analyzed crystal was determined to be a crystal of rifaximin β.

Example 10

Preparation of Crystals of Rifaximin $\alpha_0$, $\alpha_{0.5}$ and $\alpha_{1.5}$ Rifaximin crystals obtained in Example 2 were placed in a dryer at room temperature and under ambient pressure in the presence of $P_2O_5$ for 24 hours.

Rifaximin crystals were analyzed by means of X-ray diffraction using:

a) An X'calibur diffractometer by Oxford Diffraction, provided with a CCD area detector which uses MoKα radiation ($\lambda=0.71073$ Å) and a graphite monochromator; data were collected at room temperature. The structures were solved by direct methods using the SHELX97 program (Sheldrick, 2008) implemented in the WinGX package (Farrugia, 1999);

b) synchrotron ELETTRA (Trieste) at the XRD1 beam line at room temperature and at 100 K, using the cooling system MARSCH 300.

The structures were solved using the SHELX97 program (Sheldrick, 2008) implemented in the WinGX package (Farrugia, 1999).

Table 8 reports the crystallographic parameters relating to the analyzed rifaximin crystals.

These crystals were characterized in that they are crystals of rifaximin α and in that they have precise water molar ratios.

TABLE 8

|  | Crystal parameters 3 | Crystal parameters 4 | Crystal parameters 4 | Crystal parameters 5 |
| --- | --- | --- | --- | --- |
| Chemical formula | $C_{43}H_{51}N_3O_{11}$ | $C_{43}H_{51}N_3O_{11.5}$ | $C_{43}H_{51}N_3O_{11.5}$ | $C_{43}H_{54}N_3O_{12.5}$ |
| $H_2O$ molecules for each rifaximin molecule | 0 | 0.5 | 0.5 | 1.5 |
| MW | 785.87 | 794.89 | 794.89 | 812.83 |
| temperature/K | 295 | 295 | 100 | 295 |
| λ(Å) | 1 | 0.71073 | 1 | 0.71073 |
| Crystalline system | monoclinic | monoclinic | monoclinic | monoclinic |
| Space group | $P2_1$ | $P2_1$ | $P2_1$ | $P2_1$ |
| a/Å | 14.232(4) | 14.579(4) | 14.401(4) | 14.492(4) |

TABLE 8-continued

|  | Crystal parameters 3 | Crystal parameters 4 | Crystal parameters 4 | Crystal parameters 5 |
|---|---|---|---|---|
| b/Å | 19.822(4) | 20.232(4) | 19.662(4) | 20.098(4) |
| c/Å | 16.164(4) | 16.329(4) | 16.153(4) | 16.215(4) |
| β/deg | 108.74(3) | 111.21(3) | 111.04(3) | 111.21(3) |
| V/Å$^3$ | 4318.2(5) | 4402.7(5) | 4268.6(5) | 4402.7(5) |
| Z | 4 | 4 | 4 | 4 |
| $D_c$/Mg m$^{-3}$ | 1.209 | 1.237 | 1.237 | 1.226 |

Analogous results were obtained by drying under the same conditions starting from rifaximin crystals obtained in Examples 4, 6 and 8.

Example 11

Determination of Rifaximin Solubility in Ethanol-Water Solutions

A rifaximin amount corresponding to 200 mg was dissolved in 10 ml of a solution formed by ethanol/water 1:4 (v/v), left for two days under stirring at room temperature.

Rifaximin solubility was determined by wavelength spectrophotometry at wavelength 276 nm with a rifaximin calibration curve. The measured rifaximin solubility for the sample is 48 µg/ml.

Example 12

Determination of Rifaximin Solubility in Aqueous Solutions in the Presence of Amino Acids The example describes the determination of rifaximin solubility in aqueous solutions in the presence and in the absence of amino acids.

In particular, experiments are summarized in Table 9.

Experiment 1 describes the determination of the solubility obtained by placing 20 mg rifaximin in phosphate buffer at pH 6.8 (P.B.) at room temperature for 2 hours;

Experiments 2, 3 and 4 describe rifaximin solubility in water obtained by placing 200 mg rifaximin and 195 mg tryptophan, serine and histidine, respectively corresponding to molar ratios rifaximin:amino acid 1:4, 1:7.5 and 1:5, and the solutions are kept under stirring at room temperature for 24 hours.

Experiments 5-14 describe the solubility obtained by placing 20 g rifaximin in 500 ml buffer at pH 6.8 with various amino acids in molar ratios reported in Table 9, and the solutions are kept under stirring for 24 hours at 37° C. in vessel.

Rifaximin solutions are filtered and rifaximin concentrations are determined by means of calibration curve spectrophotometry, at wavelength 364 nm.

Table 9 also reports values relating to the increase of rifaximin concentrations in solutions with different amino acids if compared to respective reference solutions of rifaximin alone in water or phosphate buffer (Trials 1 and 5).

TABLE 9

| Experiment | AA | V (ml) | T (° C.) | Solution | AA/Rifax (mol/mol) | Conc. (µg/ml) | Conc. trial N./ Conc. trials 1 and 5 |
|---|---|---|---|---|---|---|---|
| 1 | — | 50 | r.t. | P.B. | — | 3.5 | 1 |
| 2 | Tryptophan | 5 | r.t. | H$_2$O | 4:1 | 35 | 10 |
| 3 | Serine | 5 | r.t. | H$_2$O | 7.5:1 | 5.7 | 1.6 |
| 4 | Histidine | 5 | r.t. | H$_2$O | 5:1 | 21.8 | 6.2 |
| 5 | — | 500 | 37° C. | H$_2$O | — | 7 | 1 |
| 6 | Tryptophan | 500 | 37° C. | P.B. | 10:1 | 22 | 3.1 |
| 7 | Tryptophan | 500 | 37° C. | P.B. | 3:1 | 30 | 4.2 |
| 8 | Tryptophan | 500 | 37° C. | P.B. | 1:1 | 21 | 3 |
| 9 | Histidine | 500 | 37° C. | P.B. | 10:1 | 16 | 2.3 |
| 10 | Histidine | 500 | 37° C. | P.B. | 3:1 | 12 | 1.7 |
| 11 | Histidine | 500 | 37° C. | P.B. | 1:1 | 10 | 1.4 |
| 12 | Valine | 500 | 37° C. | P.B. | 3:1 | 8 | 1.1 |
| 13 | Leucine | 500 | 37° C. | P.B. | 3:1 | 8 | 1.1 |
| 14 | Isoleucine | 500 | 37° C. | P.B. | 3:1 | 10 | 1.4 |

Example 13

Determination of Solubility in Water of Conglomerates of Rifaximin and Tryptophan Obtained in Example 2

The solubility of conglomerates of rifaximin and tryptophan, obtained in Example 2, was determined by placing 653 mg of this solid in 5 ml phosphate buffer at pH 6.8 at room temperature. The solution was left for 24 hours under stirring.

Rifaximin concentration in solution was determined by means of wavelength spectrophotometry at wavelength 364 nm and is 28 µg/ml.

Example 14

Determination of Rifaximin Solubility in Water and in Buffer Solutions at Various pH

Comparative Example

Rifaximin solubility values was determined by placing the rifaximin amounts respectively reported in Table 10 in a volume of 50 ml, respectively of water, phosphate buffer at pH 4, phosphate buffer at pH 7 and borate buffer at pH 10.

The suspensions were stored under nitrogen and at 30° C., under conditions of stirring, for 24 hours.

The determination of rifaximin concentration in solution was carried out by means of a chromatographic method under the conditions reported in European Pharmacopoeia Ed. 7.1, March/2011, paragraph 2362, page 3459 and the obtained results were reported in Table 10.

TABLE 10

| Trial | Solution | Rifaximin amount (mg) | Rifaximin concentration (µg/ml) |
|---|---|---|---|
| 1 | $H_2O$ | 20 | 3.63 µg/ml |
| 2 | Phosphate buffer pH 4 | 15 | 4.12 µg/ml |
| 3 | Phosphate buffer pH 7 | 20 | 3.22 µg/ml |
| 4 | Borate buffer pH 10 | 65 | 299 µg/ml |

Example 15

Determination of Rifaximin Dissolution Profile in Coated Tablets and Tablets Comprising Gastroresistant Microgranules Comparative Example The dissolution profiles for commercially available coated tablets NORMIX®, comprising 200 mg rifaximin, and tablets comprising 400 mg rifaximin in gastroresistant microgranules were determined under the conditions reported in European Pharmacopoeia, Ed. 7.1, paragraph 2.9.3, page 256-263. Rifaximin quantitative determination was obtained under the conditions described in European Pharmacopoeia, Ed. 7.1, March/2011, paragraph 2362, page 3459.

Dissolution profiles of NORMIX® tablets and of rifaximin tablets in gastroresistant microgranules were determined in solutions at pH 5 and pH 6.5 as well as in FaSSIF solutions and FeSSIF solutions.

The FaSSIF solution contains taurocholate sodium, 3 mM; lecithin, 0.75 mM; NaH2PO4, 65 mM, NaCl 85 mM, and purified water up to 1 l, with a pH 6.5.

The FeSSIF solution contains taurocholate sodium 15 mM, lecithin 3.75 mM, glacial acetic acid 144.05 mM, NaCl 203.18 mM, and purified water up to 1 l, with a pH 5.

The dissolution profiles reported in Table 11 were determined by using two NORMIX® tablets and a rifaximin tablet in gastroresistant microgranules, in buffer pH 5, buffer pH 6.5, FaSSIF solution and FeSSIF solution, for 360 minutes.

The dissolution profiles of the 2 of NORMIX® tablets and of the rifaximin tablet in gastroresistant microgranules are reported in Table 11.

TABLE 11

|  | Rifaximin Normix ® tablets Rifaximin concentration (µg/ml) | Rifaximin tablets in gastroresistant microgranules Rifaximin concentration (µg/ml) |
|---|---|---|
| Buffer pH 5 | 6.67 ± 0.29 | 4.49 ± 0.23 |
| Buffer pH 6.5 | 6.09 ± 1.01 | 9.56 ± 0.81 |
| FaSSIF | 8.40 ± 0.56 | 13.78 ± 0.64 |
| FeSSIF | 11.73 ± 1.99 | 20.58 ± 3.27 |

Example 16

Preparation of Granules Comprising Rifaximin and Amino Acids

An amount of 200 g of rifaximin, amino acids, hydroxypropyl methylcellulose, fumed silica and talc were mixed in a V mixer for 15 min at a speed of 16 rpm. The solid mixtures were loaded in a roller compactor with an applied pressure of up to 100 bar.

The granule composition is reported in Table 12.

TABLE 12

| Component | Granule 1 (grams) | Granule 2 (grams) | Granule 3 (grams) |
|---|---|---|---|
| Rifaximin | 200 | 200 | 200 |
| Tryptophan | 195 | — | — |
| Serine | — | 75 | — |
| Histidine | — | — | 145 |
| Hydroxypropyl methylcellulose | 84.6 | 104.6 | 134.6 |
| Fumed silica | 0.4 | 0.4 | 0.4 |
| Talc | 20 | 20 | 20 |

The granules so obtained can be coated with coating film or gastroresistant film and used for suspension or tablet preparations.

Example 17

Preparation of Granules Comprising Rifaximin and Amino Acids

An amount of 200 g rifaximin and amino acids, hydroxypropyl methylcellulose, fumed silica and talc were mixed in a V mixer for 15 min at a speed of 16 rpm. The solid mixtures were loaded in a roller compactor with an applied pressure up to 100 bar.

The granule composition is reported in Table 13.

TABLE 13

| Component | Granule 4 (grams) | Granule 5 (grams) | Granule 6 (grams) |
|---|---|---|---|
| Rifaximin | 200 | 200 | 200 |
| Tryptophan | 195 | 195 | 195 |
| valine | 117 | — | — |
| leucine | — | 131 | — |
| Isoleucine | — | — | 131 |
| Hydroxypropyl methylcellulose | 84.6 | 104.6 | 134.6 |
| Fumed silica | 0.4 | 0.4 | 0.4 |
| Talc | 20 | 20 | 20 |

The granules so obtained can be coated with coating film or gastroresistant film and used for suspension or tablet preparations.

Example 18

Preparation of Sachets Comprising Granules of Amino Acid and Rifaximin

The granules obtained according to Example 16 and 17 were added to the excipients listed in Table 14, and the resulting solid mixtures were divided in sachets. The sachet unitary composition is reported in Table 14.

TABLE 14

| Component | Sachet 1 (mg) | Sachet 2 (mg) | Sachet 3 (mg) | Sachet 4 (mg) | Sachet 5 (mg) | Sachet 6 (mg) |
|---|---|---|---|---|---|---|
| Granule 1 Example 16 | 500 | | | | | |
| Granule 2 Example 16 | | 400 | | | | |
| Granule 3 Example 16 | | | 500 | | | |
| Granule 4 Example 17 | | | | 500 | | |
| Granule 5 Example 17 | | | | | 400 | |
| Granule 6 Example 17 | | | | | | 500 |
| Hydrophobic Colloidal Silica | 10 | 10 | 10 | 10 | 10 | 10 |
| Aspartame | 20 | 20 | 20 | 20 | 20 | 20 |
| Cherry-flavour | 100 | 100 | 100 | 100 | 100 | 100 |
| Sobitol | 3370 | 3470 | 3370 | 3370 | 3470 | 3370 |
| TOT | 4000 | 4000 | 4000 | 4000 | 4000 | 4000 |

Example 19

Preparation of Tablets Comprising Rifaximin and Amino Acids

Rifaximin granule prepared as in Example 16 and 17 were mixed with excipients, and all of the components were mixed in a V binder. The resulting mixtures were compressed in a tabletting machine. The tablets were coated with film coating.

The unitary composition of tablets is reported in Table 15.

TABLE 15

| Components | Tablet 1 (mg) | Tablet 2 (mg) | Tablet 3 (mg) | Tablet 4 (mg) | Tablet 5 (mg) | Tablet 6 (mg) |
|---|---|---|---|---|---|---|
| Granule 1 Example 16 | 500 | | | | | |
| Granule 2 Example 16 | | 400 | | | | |
| Granule 3 Example 16 | | | 500 | | | |
| Granule 4 Example 17 | | | | 500 | | |
| Granule 5 Example 17 | | | | | 400 | |
| Granule 6 Example 17 | | | | | | 500 |
| Sodium starch glycolate | 15 | 15 | 15 | | | |
| Colloidal silica | 1 | 1 | 1 | | | |
| Talc | 1 | 1 | 1 | | | |
| Coating film | | | | | | |
| Hydroxypropyl methylcellulose | 5.15 | 5.15 | 5.15 | 5.15 | 5.15 | 5.15 |
| Titanium dioxide | 1.5 | 1.5 | 1.5 | 1.5 | 1.5 | 1.5 |
| Disodium edetate | 0.02 | 0.02 | 0.02 | 0.02 | 0.02 | 0.02 |
| Propylene glycol | 0.5 | 0.5 | 0.5 | 0.5 | 0.5 | 0.5 |
| Red iron oxide E172 | 0.15 | 0.15 | 0.15 | 0.15 | 0.15 | 0.15 |

The excipients were sieved and then mixed with rifaximin granules; the resulting mixtures were compressed using a rotary tabletting machine equipped with oblong and tablets were obtained.

The tablets were coated using conventional pan equipment, in order to improve appearance and achieve taste mask properties.

The tablet can also be coated also with gastroresistant film coating.

Example 20

Preparation of Conglomerates of Rifaximin and Amino Acids

Conglomerate A: Rifaximin-Tryptophan 1:4. A volume of 5 ml ethanol/water 1:4 (v/v) solution was added to composition A—Example 1; the mixture was then heated at 100° C. until complete dissolution and left for complete solvent evaporation at room temperature for 4 days. Rifaximin conglomerates characterized by the contemporary presence of rifaximin crystals and tryptophan crystals were obtained.

Conglomerate B: Rifaximin-Serine 1:3. A volume of 5 ml ethanol/water 1:4 (v/v) solution was added to composition B—Example 1. The solution was then heated at 100° C. until complete dissolution, and left for complete solvent evaporation at room temperature for 4 days. Rifaximin conglomerate was characterized by the presence of rifaximin crystals and serine crystals.

Conglomerate C: Rifaximin-Histidine 4-1. A volume of 5 ml ethanol/water 1:4 (v/v) solution was added to composition C—Example 1. The mixture was then heated at 100° C. until reaching complete dissolution, and left for spontaneous evaporation at room temperature for 4 days. Rifaximin conglomerate characterized by the presence of rifaximin crystals and histidine crystals were obtained.

Conglomerate D: Rifaximin-Histidine 4:1. A volume of 5 ml ethanol/water 1:4 (v/v) solution was added to composition D—Example 1. The solution was then heated at 100° C. until complete dissolution, and left for spontaneous evaporation at room temperature for 4 days. Rifaximin conglomerate characterized by the presence of rifaximin crystals and histidine crystals were obtained.

Example 21

Determination of Water Solubility of Rifaximin Conglomerates

The solubility of conglomerates A, obtained according to Example 20, was determined by placing 653 mg of this solid in 5 ml phosphate buffer at pH 6.8 at room temperature. The solution was left for 24 hours under stirring.

Rifaximin concentration in solution was determined by spectrophotometric method at wavelength 364 nm. The rifaximin concentration was 28 µg/ml.

The invention claimed is:

1. A pharmaceutical composition comprising rifaximin or one of the pharmaceutically acceptable salts thereof and one or more aromatic amino acid or a heterocyclic amino acid(s), wherein the molar ratio between the amino acid(s) and rifaximin is from 1:1 to 10:1, together with one or more pharmaceutically acceptable excipients.

2. The pharmaceutical composition according to claim 1, wherein the molar ratio between the amino acid(s) and rifaximin is from 1:1 to 5:1.

3. The pharmaceutical composition according to claim 1, wherein the rifaximin is present in the pharmaceutical composition as a crystalline, polymorphous, amorphous, hydrate, or solvate form or as a mixture thereof.

4. The pharmaceutical composition according to claim 3, wherein the crystalline form of rifaximin is selected from
  i) a form having monoclinic space group P2₁ and cell parameters in the ranges: a: 13.7(1)-13.8(1) Å; b: 19.7(1)-19.9 (1) Å; c: 16.4(6)-16.6(6) Å; β: 92.1(1)-91.9(1) deg.,
  ii) the form of i) comprising 3 or 4.5 water molecules for each rifaximin molecule,
  iii) a form having monoclinic space group P2₁ and cell parameters in the ranges: a: 14.2(1)-14.5(1) Å; b: 19.7(1)-20.1(1) Å; c: 16.1(1)-16.2(1) Å; β: 108.7(1)-111.4(1) deg.
  iv) the form of iii) comprising zero or 0.5 or 1.5 water molecules for each rifaximin molecule, or
  v) a form of rifaximin α, β, γ, or δ.

5. The pharmaceutical composition according to claim 1, wherein rifaximin is in a dosage from 20 mg to 1200 mg.

6. The pharmaceutical composition according to claim 1, wherein the one or more amino acid(s) further comprise one or more amino acid(s) is/are selected from the group consisting of aliphatic amino acids, basic amino acids, branched amino acids, cyclic amino acids, acidic amino acids, hydroxyl or sulfur containing amino acids, amide amino acids and mixtures thereof.

7. The pharmaceutical composition according to claim 1, wherein the one or more amino acid(s) is/are selected from histidine, tryptophan, phenyl alanine, tyrosine, and proline.

8. The pharmaceutical composition according to claim 6, wherein the one or more further comprised amino acid(s) is/are branched amino acids.

9. The pharmaceutical composition according to claim 1, wherein the one or more further comprised amino acid(s) are selected from valine, leucine and isoleucine; and wherein the molar ratio between the amino acids and rifaximin is 10:1.

10. The pharmaceutical composition according to claim 1, wherein the pharmaceutically acceptable excipients include one or more of: diluting agents, binding agents, disintegrating agents, lubricating agents, release-controlling polymers and bioadhesive polymers.

11. The pharmaceutical composition of claim 10, wherein the diluting agent is at least one selected from the group consisting of: cellulose, microcrystalline cellulose, calcium phosphate, starch, kaolin, dehydrated calcium sulphate, calcium carbonate, lactose, saccharose, glucose, sorbitol and mannitol.

12. The pharmaceutical composition of claim 10, wherein the binding agent is at least one selected from the group consisting of: cellulose, cellulose derivatives, carboxy methyl cellulose, microcrystalline cellulose, hydroxy propyl cellulose, hydroxy ethyl cellulose, hydroxy propyl-methyl cellulose, starches, potato starch, maize starch, partially gelatinized starch, gums, synthetic gum, natural gums, polyvinyl pyrrolidone, polyethylene glycol, gelatin, polyols, propylene glycol, alginates and sugars.

13. The pharmaceutical composition of claim 10, wherein the disintegrating agent is at least one selected from the group consisting of: sodium carboxy methyl cellulose, cross-linked sodium carboxy methyl cellulose, polyvinyl pyrrolidone, cross-linked polyvinyl pyrrolidone, starch, pregelatinized starch and silica.

14. The pharmaceutical composition of claim 10, wherein the lubricating agent is at least one selected from the group consisting of: silica, magnesium stearate, calcium stearate, sodium stearyl fumarate, hydrogenated vegetable oils, mineral oils, polyethylene glycols, sodium lauryl sulphate, glycerides, sodium benzoate, glyceryl dibehenate and glycerol stearate.

15. The pharmaceutical composition of claim 10, wherein the release-controlling polymer is at least one selected from the group consisting of: copolymers of acrylic acid, copolymers of methacrylic acid with an acrylic or methacrylic ester, polyvinyl acetate phthalate, hydroxy propyl methyl cellulose phthalate, cellulose acetate phthalate, Kollicoat®, Eudragit®, Aquateric®, Aqoat®; natural polymers and ethyl cellulose.

16. The pharmaceutical composition of claim 10, wherein the bioadhesive polymer is at least one selected from the group consisting of: pectins, zeins, casein, gelatin, albumin, collagen, kitosan, cellulose, dextran, polysaccharides from tamarind seeds, xanthan gum, arabic gum, hyaluronic acid, alginic acid, sodium alginate, polyamides, polycarbonates, polyalkylenes, polyalkylene glycols, polyalkylene oxides, polyalkylene terephthalates, polyvinyl alcohols, polyvinyl ethers, polyvinyl esters, polyvinyl pyrrolidone, polysiloxanes, polyurethanes, polystyrenes, polymers of acrylic acid and methacrylic esters, copolymers of methacrylic acid-ethyl acrylate, polylactides, barbituric polyacids, polyanhydrides, polyorthoesters, methyl cellulose, ethyl cellulose, hydroxy propyl cellulose, hydroxy butyl methyl cellulose, cellulose acetate, cellulose propionate, cellulose acetate butyrate, cellulose acetate phthalate, carboxy methyl cellulose, cellulose triacetate, cellulose sulfate sodium salt, polymethyl methacrylate, poly isobutyl acrylate, poly octadecyl acrylate, polypropylene, polyethylene glycol, polyethylene oxide, polyethylene terephthalate, polyvinyl acetate, polyvinyl chloride, polystyrene, polyvinyl phenol, carboxylic acids, sulphonic acids, phosphonic acids, and neutral and positively charged amines, amides and imines.

17. The pharmaceutical composition according to claim 1, wherein the composition is in the form of a powder, paste, tablet, capsule, ovules cream, foam, suspension, solution, aerosol, granulates, ointment or suppository suitable for human or animal administration.

18. The pharmaceutical composition according to claim 17, wherein the composition is in a form for oral or vaginal or topical administration.

19. The pharmaceutical composition of claim 18, wherein the composition includes rifaximin in an amount from 20 to 1200 mg.

20. The pharmaceutical composition of claim 19, wherein the composition includes rifaximin in an amount from 100 to 600 mg.

21. The pharmaceutical composition according to claim 1, wherein the one or more pharmaceutically acceptable excipients are selected from the group consisting of edulcorating agents, coloring agents, anti-oxidizing agents, buffering agents and flavoring agents.

22. The pharmaceutical composition according to claim 21, wherein the edulcorating agent is at least one selected from the group consisting of potassium acesulfame, sorbitol, mannitol, isomalt, maltitol, lactitol, xylitol, aspartame, cyclamic acid, cyclamate salts, lactose, sucralose, saccharine and saccharine salts.

23. A process for the production of rifaximin crystals, said process comprising:
  a) dissolving rifaximin and one or more aromatic or heterocyclic amino acids, wherein the amino acids and rifaximin are in a molar ratio from 1:1 to 10:1 in a solution consisting of ethanol and water in a volumetric ratio from 1:1 to 1:10 (v/v);
  b) evaporating the solution obtained in step a) to obtain rifaximin crystals.

24. The process according to claim 23, wherein the evaporation of the solution takes place at temperatures from room temperature to 40° C.

25. The process according to claim 23, wherein the evaporation of the solution takes place in a time period from 1 to 10 days.

26. The process according to claim 23, wherein the resulting crystals are characterized by monoclinic space group $P2_1$ and cell parameters comprised in the ranges:
   a: 13.7(1)-13.8(1) Å; b: 19.7(1)-19.9 (1) Å; c: 16.4(6)-16.6(6) Å; β: 92.1(1)-91.9(1) deg.

27. The process according to claim 23, wherein evaporating the solution is performed in the presence of dehydrating agents.

28. The process according to claim 27, wherein the evaporation of the solution takes place at temperatures from room temperature to 40° C.

29. The process according to claim 23, wherein the evaporation of the solution takes place in a time period from 1 to 10 days.

30. The process according to claim 27, wherein the resulting crystals have monoclinic space group $P2_1$ and cell parameters comprised in the ranges:
   a: 14.2(1)-14.5(1) Å; b: 19.7(1)-20.1(1) Å; c: 16.1(1)-16.2(1) Å; β: 108.7(1)-111.4(1) deg.

31. A composition comprising one or more aromatic or heterocyclic amino acids and rifaximin wherein the molar ratio between the amino acids and rifaximin is from 1:1 to 10:1.

32. The composition according to claim 31, in the form of an aqueous solution and wherein the rifaximin concentration is from 4.5 μg/ml to 60 μg/ml at room temperature.

33. The composition according to claim 31, wherein said composition is in the form of a conglomerate.

34. The composition according to claim 32, wherein the aqueous solution further comprises one or more organic solvents in an amount from 1% to 25% v/v.

* * * * *